United States Patent
Douglas et al.

(10) Patent No.: US 10,956,635 B1
(45) Date of Patent: Mar. 23, 2021

(54) RADIOLOGIST-ASSISTED MACHINE LEARNING WITH INTERACTIVE, VOLUME SUBTENDING 3D CURSOR

(71) Applicants: David Byron Douglas, Winter Park, FL (US); Kathleen Mary Douglas, Winter Park, FL (US); Robert Edwin Douglas, Winter Park, FL (US)

(72) Inventors: David Byron Douglas, Winter Park, FL (US); Kathleen Mary Douglas, Winter Park, FL (US); Robert Edwin Douglas, Winter Park, FL (US)

( * ) Notice: Subject to any disclaimer, the term of this patent is extended or adjusted under 35 U.S.C. 154(b) by 0 days.

(21) Appl. No.: 16/703,629

(22) Filed: Dec. 4, 2019

(51) Int. Cl.
*G06F 30/23* (2020.01)
*G06T 7/00* (2017.01)
*G06T 15/08* (2011.01)
*G06T 17/20* (2006.01)
*G06F 17/18* (2006.01)
*G06N 20/20* (2019.01)
*G06T 7/10* (2017.01)

(52) U.S. Cl.
CPC .............. *G06F 30/23* (2020.01); *G06F 17/18* (2013.01); *G06N 20/20* (2019.01); *G06T 7/0012* (2013.01); *G06T 7/10* (2017.01); *G06T 15/08* (2013.01); *G06T 17/205* (2013.01); *G06T 2207/20081* (2013.01); *G06T 2210/41* (2013.01)

(58) Field of Classification Search
CPC .................................................. G06T 7/0002
USPC .......................................................... 345/419
See application file for complete search history.

(56) References Cited

U.S. PATENT DOCUMENTS

| 10,210,631 | B1* | 2/2019 | Cinnamon | G06T 11/003 |
| 10,496,809 | B1* | 12/2019 | Pham | G06N 3/088 |
| 2017/0319156 | A1* | 11/2017 | Hong | A61B 6/547 |
| 2018/0046763 | A1* | 2/2018 | Price, Jr. | G06F 19/324 |
| 2018/0260957 | A1* | 9/2018 | Yang | G06T 7/143 |
| 2018/0336677 | A1* | 11/2018 | Sloan | G06T 7/30 |
| 2019/0099159 | A1* | 4/2019 | Voigt | G06T 7/60 |
| 2019/0164288 | A1* | 5/2019 | Wang | G06T 5/002 |
| 2019/0216409 | A1* | 7/2019 | Zhou | A61B 6/032 |
| 2019/0220977 | A1* | 7/2019 | Zhou | G06T 5/50 |
| 2019/0251713 | A1* | 8/2019 | Chen | G06N 3/084 |
| 2019/0261945 | A1* | 8/2019 | Funka-Lea | A61B 8/145 |
| 2019/0266728 | A1* | 8/2019 | Lee | A61B 5/7221 |
| 2019/0369191 | A1* | 12/2019 | Gong | G16H 50/50 |
| 2020/0129784 | A1* | 4/2020 | Beriault | A61N 5/1067 |

\* cited by examiner

*Primary Examiner* — David T Welch

(57) ABSTRACT

This patent includes a method and apparatus for the generation of a simulated, realistic 3D radiological dataset from CT, MRI, PET, SPECT or DTS examinations. This simulated dataset can be segmented, filtered, manipulated, used with artificial intelligence algorithms and viewed in conjunction with head display units and geo-registered tools.

20 Claims, 28 Drawing Sheets

ILLUSTRATION OF THE KEY COMPONENTS FOR AN INTEGRATED
RADIOLOGIST-ASSISTED MACHINE LEARNING PROCESS

ILLUSTRATION OF 3D CURSOR USE IN CONJUNCTION WITH RADIOLOGIST-ASSISTED MACHINE LEARNING
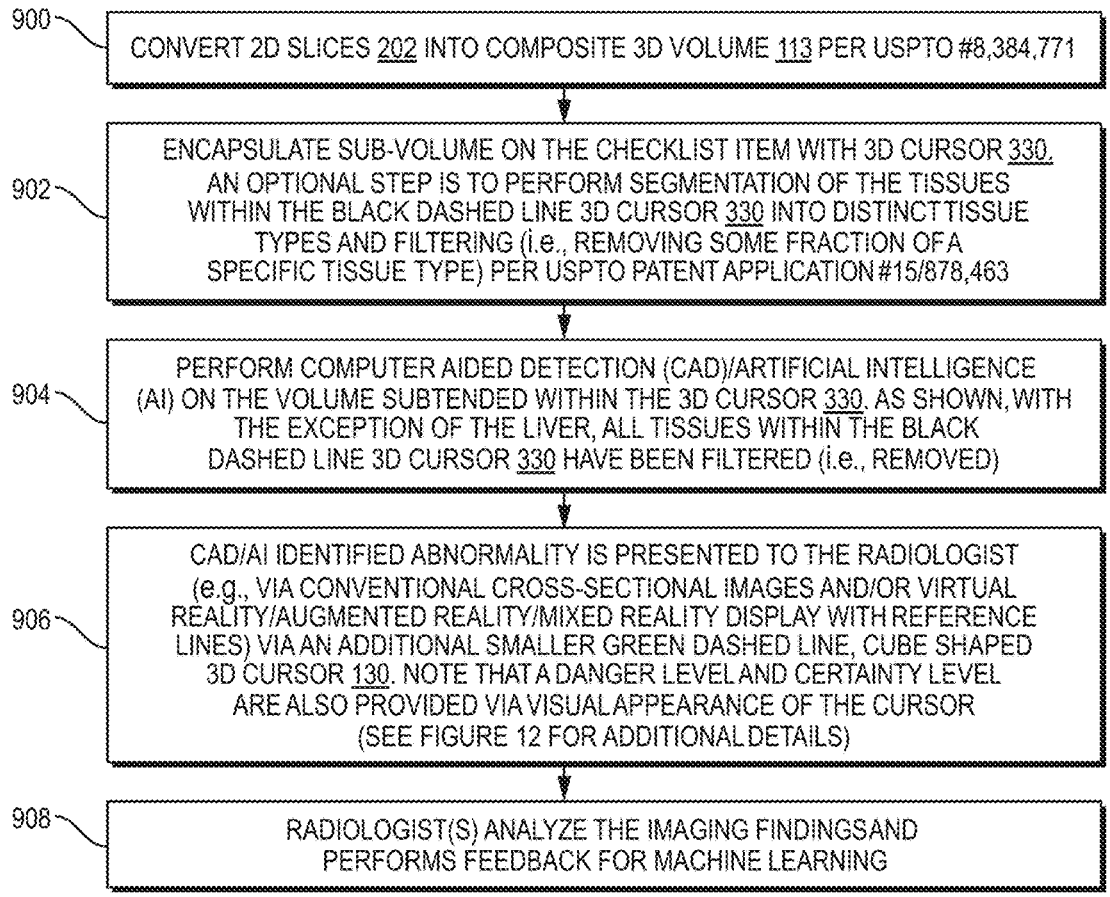
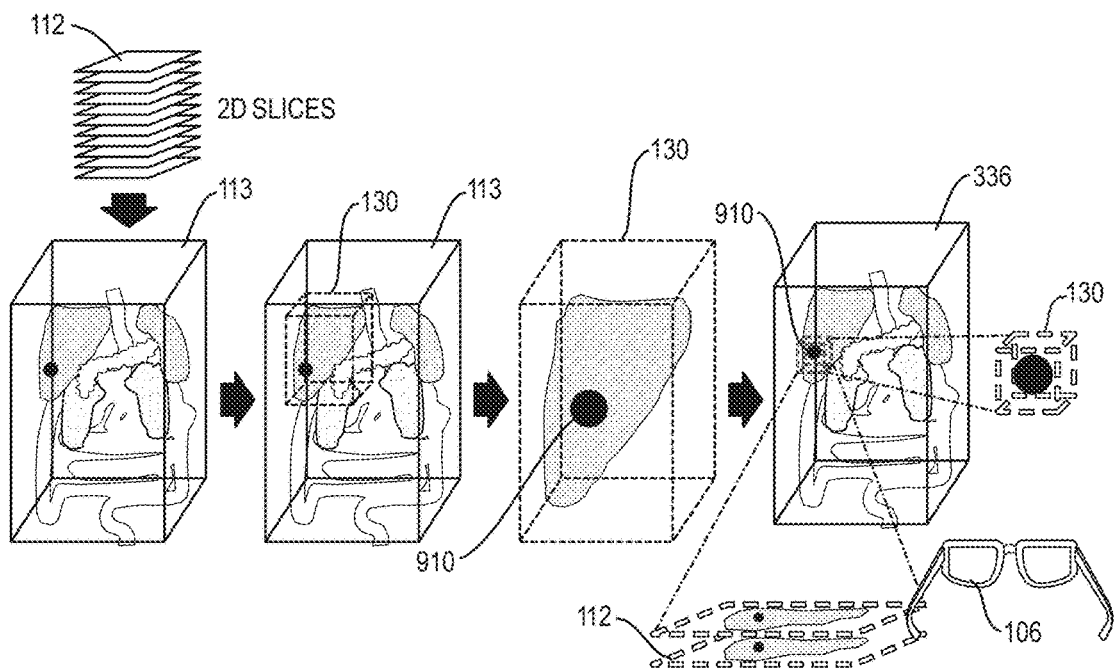
FIG. 9

ILLUSTRATION OF THE RELATIONSHIP BETWEEN THE COMPOSITE
VOLUME, A SUB-VOLUME AND VOLUME SUBTENDING 3D CURSOR

Exam: CT Abdomen/Pelvis
Patient Name: ##########
Date of Birth: ##########
Medical Record Number: ##########
Accession Number: ##########
Indication for exam: Acute right flank pain
AI identified history: Microhematuria
Comparisons: None
Technique: Noncontrast CT scan of the abdomen and pelvis was performed.

Radiation Dose: #####
Findings:

| | | | |
|---|---|---|---|
| Lungs: | Negative | | |
| Heart: | Negative | | For this finding, the radiologist agreed with AI diagnosis, management and imaging recommendations. There is a 1 cm spherical, fluid-density lesion located in the liver, most likely representing a simple cyst. This is an incidental, benign finding and no management action or follow up is required. |
| Liver: | Positive | 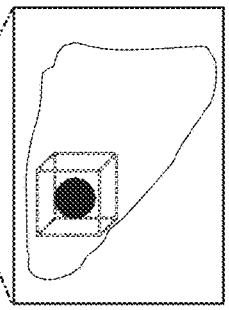 | |
| Gallbladder: | Negative | | |
| Spleen: | Negative | | |
| Pancreas: | Negative | | |
| Adrenal glands: | Negative | | |
| Kidneys: | Negative | | |
| Ureters: | Positive | | For this finding, the radiologist agreed with AI diagnosis, management and imaging recommendations. A calcified stone measuring 0.3 is located in the distal ureter 1 cm proximal to the ureterovesicular junction. No hydroureteronephrosis. Recommend urology consultation and follow up CT Abdomen/Pelvis exam as needed. |
| Bladder: | Negative | | |
| Esophagus: | Negative | | |
| Stomach: | Negative | 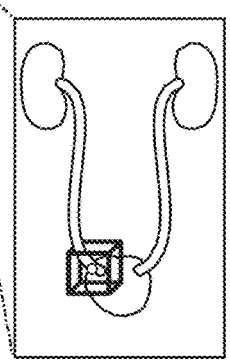 | |
| Small bowel: | Negative | | |
| Colon: | Negative | | |
| Rectum: | Negative | | |
| Vasculature: | Negative | | |
| Lymph nodes: | Negative | | |
| Bones: | Negative | | |
| Muscles: | Negative | | |
| Subcutaneous fat: | Negative | | |

Impression:
A calcified stone measuring 0.3 is located in the distal ureter 1 cm proximal to the ureterovesicular junction. No hydroureteronephrosis. Recommend urology consultation and follow up CT Abdomen/Pelvis exam as needed.

FIG. 15

Simulation of MRI, CT, PET, SPECT or DTS medical image data through establishing a 3D grid system and associated X, Y, Z coordinate system
2100

A mathematical process to populate a 3D volume with simulated data corresponding to and representative of MRI, CT, PET or DTS medical images
2102

Assigning a tissue type property to each voxel within the simulated dataset
2104

Potting and displaying the simulated 3D MRI, CT, PET or DTS data
2106

Establishing the 3D cursor with associated functionality
2108

Establishing the process by which the 3D volume of simulated data can be segmented
2110

Establishing the process by which the 3D volume of simulated data can be filtered
2112

Establishing the geo-registered tools with associated functionality
2114

Establishing the adjudication process for times when radiologists/ medical personnel diagnoses conflict with AI algorithm diagnoses
2116

Implementing the overall system functionality
2118

FIG. 21

OVERVIEW OF THE APPARATUS

2800

| Top Slice | Transverse direction | | | | | |
|---|---|---|---|---|---|---|
| Anterior-posterior direction | | column 1 | column 2 | column 3 | column 4 | column 5 |
| | row 1 | -100 | -105 | -95 | -91 | -90 |
| | row 2 | -106 | -89 | -79 | -92 | -98 |
| | row 3 | -95 | -92 | -89 | -85 | -97 |

2802

| Bottom Slice | Transverse direction | | | | | |
|---|---|---|---|---|---|---|
| Anterior-posterior direction | | column 1 | column 2 | column 3 | column 4 | column 5 |
| | row 1 | -102 | -97 | -91 | -101 | -99 |
| | row 2 | -101 | -92 | -84 | -104 | -90 |
| | row 3 | -94 | -96 | -92 | -89 | -94 |

FIG. 28

RADIOLOGIST-ASSISTED MACHINE LEARNING WITH INTERACTIVE, VOLUME SUBTENDING 3D CURSOR

CROSS REFERENCE TO RELATED APPLICATIONS

The present application is a continuation-in-part of PCT/US19/47891, filed on 26 Mar. 2019, which claims the benefit of U.S. Provisional Application No. 62/748,555, filed on 22 Oct. 2018, U.S. Provisional Application No. 62/651,934, filed on 3 Apr. 2018, and U.S. Provisional Application No. 62/776,234, filed on 6 Dec. 2018, the disclosures of which are incorporated herein by reference in their entirety.

TECHNICAL FIELD

Aspects of this disclosure are generally related to use of computer aided detection (CAD) and artificial intelligence (AI) in the medical field, and more particularly to machine learning in diagnostic radiology.

BACKGROUND

AI and CAD are quickly changing the field of medical imaging. As an example, many mammographers use CAD to help detect breast cancer on 2D imaging. However, CAD systems have limitations including lack of optimization for clinical impact and lack of quantification of performance efficiency.

SUMMARY

All examples, aspects and features mentioned in this document can be combined in any technically conceivable way.

In accordance with an aspect a method comprises: continuously updating a training dataset while analyzing medical image data with a medical image diagnostic computer having machine-learning capability, comprising the steps of: using a three-dimensional cursor to select a sub-volume of a medical image, wherein the selected sub-volume corresponds to an item on a diagnostic checklist; analyzing the selected sub-volume to create a human-generated analysis; and using the human-generated analysis to update the training dataset. Some implementations comprise analyzing the selected sub-volume using the training dataset to create a machine-generated analysis with the diagnostic computer before manually analyzing the selected sub-volume. Some implementations comprise resolving disagreement between the human-generated analysis and the machine-generated analysis before using the human-generated analysis to update the training dataset. Some implementations comprise generating a computer-made explanation for the machine-generated analysis. Some implementations comprise updating the human-generated analysis based on the explanation before using the human-generated analysis to update the training dataset. Some implementations comprise prompting a consensus review of the human-generated analysis and machine-generated analysis. Some implementations comprise updating the human-generated analysis based on the consensus review before using the human-generated analysis to update the training dataset. Some implementations comprise the diagnostic computer retrieving and presenting patient-specific data pertinent to the item on the checklist to facilitate creation of the human-generated analysis. In some implementations creating the human-generated analysis comprises creating at least one of: terminology describing findings or diagnosis; marked pixels or voxels; and an indication of certainty of the findings or diagnosis. In some implementations creating the machine-generated analysis comprises creating at least one of: terminology describing findings or diagnosis; marked pixels or voxels; and an indication of certainty of the findings or diagnosis. Some implementations comprise performing segmentation on tissue within the selected sub-volume. Some implementations comprise filtering out tissue within the selected sub-volume that is not associated with a finding. Some implementations comprise automatically re-sizing the three-dimensional cursor to encompass tissue associated with the finding. In some implementations the checklist comprises multiple items, each of which is analyzed, and the method comprises generating a report based on the human-generated analysis. Some implementations comprise including an indication of disagreement between the human-generated analysis and the machine-generated analysis. Some implementations comprise the three-dimensional cursor visually indicating confidence or dangerousness of a diagnosis. Some implementations comprise placing tissue associated with a finding in a virtual container. Some implementations comprise selecting a virtual container from a normal finding container, a disease-specific container, and differential diagnosis container.

In accordance with an aspect an apparatus comprises: a medical image diagnostic computer having machine-learning capability, the diagnostic computer comprising a non-transitory medium on which is stored computer program logic that continuously updates a training dataset while analyzing medical image data with, comprising: item selection logic that selects a sub-volume of a medical image with a three-dimensional cursor, wherein the selected sub-volume corresponds to an item on a diagnostic checklist; input logic that receives input that creates a human-generated analysis of the selected sub-volume; and update logic that updates the training dataset based on the human-generated analysis. Some implementations comprise diagnostic logic that analyzes the selected sub-volume using the training dataset to create a machine-generated analysis before the human-generated analysis is generated. Some implementations comprise resolution logic that resolves disagreement between the human-generated analysis and the machine-generated analysis before the human-generated analysis is used to update the training dataset. Some implementations comprise virtual guru logic that generates a computer-made explanation for the machine-generated analysis. In some implementations the resolution logic updates the human-generated analysis based on the explanation before using the human-generated analysis to update the training dataset. In some implementations the resolution logic prompts a consensus review of the human-generated analysis and machine-generated analysis. In some implementations the resolution logic updates the human-generated analysis based on the consensus review before using the human-generated analysis to update the training dataset. Some implementations comprise the diagnostic computer retrieving and presenting patient-specific data pertinent to the item on the checklist to facilitate creation of the human-generated analysis. In some implementations the human-generated analysis comprises at least one of: terminology describing findings or diagnosis; marked pixels or voxels; and an indication of certainty of the findings or diagnosis. In some implementations the machine-generated analysis comprises at least one of: terminology describing findings or diagnosis; marked pixels or voxels; and an indication of certainty of the findings or diagnosis. Some implementations comprise segmentation logic that segments tissue within the selected sub-volume. Some implementations comprise filtering logic that removes from an image tissue within the selected sub-volume that is not associated with a finding. Some implementations comprise logic that re-sizes the three-dimensional cursor to encompass tissue associated with the finding. In some implementations the checklist comprises multiple items, each of which is analyzed, and the method comprises logic that generates a report based on the human-generated analysis. In some implementations the logic that generates the report includes an indication of disagreement between the human-generated analysis and the machine-generated analysis in the report. Some implementations comprise the three-dimensional cursor visually indicating confidence or dangerousness of a diagnosis. Some implementations comprise a virtual container in which tissue associated with a finding is placed. In some implementations the virtual container is selected from a normal finding container, a disease-specific container, and differential diagnosis container.

Many researchers have attempted to apply Artificial Intelligence (AI) to diagnostic radiology images (e.g., radiographs, magnetic resonance imaging (MRI), computed tomography (CT), positron emission tomography (PET), single photon emission computed tomography (SPECT) and digital tomosynthesis (DTS)). These attempts have yielded mixed results. For example, a large study using computer aided detection (CAD) in mammography was found to lower specificity, but did not significantly improve sensitivity (Fenton J J, et al. Effectiveness of computer-aided detection in community mammography practice. Journal of the National Cancer institute. 2011).

Within the field of medicine, the inventors of this patent anticipate that diagnostic radiology will benefit greatly from augmented reality and virtual reality due to the ability to achieve true 3D stereoscopic imaging as taught in U.S. Pat. No. 8,384,771, METHOD AND APPARATUS FOR THREE DIMENSIONAL VIEWING OF IMAGES. A further benefit is focal point convergence as taught in U.S. Pat. No. 9,349,183, METHOD AND APPARATUS FOR THREE DIMENSIONAL VIEWING OF IMAGES. A further benefit is 3D cursor usage as taught in U.S. Pat. No. 9,980,691, METHOD AND APPARATUS FOR THREE DIMENSIONAL VIEWING OF IMAGES. A further benefit is an advanced filtering and segmentation algorithms, U.S. patent application Ser. No. 15/904,092, PROCESSING 3D MEDICAL IMAGES TO ENHANCE VISUALIZATION. A further benefit is the use of geo-registered tools, U.S. Patent Application 62/711,658, A METHOD AND APPARATUS FOR USE OF GEO-REGISTERED TOOLS TO OPTIMIZE DISPLAY OF 3D MEDICAL IMAGING EXAMS. A further benefit is the use of virtual tools (USPTO Application 62/722,513), VIRTUAL TOOL KIT FOR RADIOLOGISTS. A further benefit is allowing voxel manipulation to facilitate in simulations for improved viewing, U.S. Patent Application 62/695,868, INTERACTIVE VOXEL MANIPULATION STRATEGIES IN VOLUMETRIC MEDICAL IMAGING ENABLES VIRTUAL MOTION, DEFORMABLE TISSUE, AND VIRTUAL RADIOLOGICAL DISSECTION. A further benefit is a method by which a digital breast tomosynthesis dataset can be processed into a 3D dataset, U.S. Patent Application 62/743,837, METHOD AND APPARATUS FOR PERFORMING 3D IMAGING EXAMINATIONS OF A STRUCTURE UNDER DIFFERENT CONFIGURATIONS AND ANALYZING MORPHOLOGIC CHANGES. Specifically, the methods disclosed herein help to overcome the significant difficulty, which AI algorithms experience in detecting for small diagnostic features in the midst of large sets of data. For example, an MRI of the breast may have millions of pixels in the collective axial, coronal, and sagittal views and only a few dozed may be tissue of concern. It is important to detect these structures in the early stages when the cancer is small (e.g., Stage 1 or 2 tumor) to reduce treatment costs, but most importantly to improve survival and reduce morbidity.

This patent provides a method to generate simulated 3D radiological datasets (e.g., MRI, CT, PET, SPECT and DTS) data and associated 2D image slices thereof. The sizes, shapes, features, location and orientation of the various tissue structures could be modified an arbitrarily large number of times, so as to keep the most realistic cases. An example of a process that could be used to generate and discriminate real vs. fake data are generative adversarial networks. This data could then be used to train and test AI algorithms and also to train and test radiologists/medical personnel. Hospitals or other entities could retain a repository of the simulated data for reference purposes. The types of simulated data include, but are not limited to: normal examinations of patients of varying ages; cerebral aneurysms; brain tumors; strokes; clusters of microcalcifications within the breast; lung cancers; nondisplaced fractures; hepatic steatosis; renal calculi; colon polyps; mitral valve regurgitation; atherosclerotic disease; and, deep vein thrombosis in a leg. These are but examples and the list of possible conditions goes on and on.

Some implementations comprise but, are not limited an apparatus comprised of a computer system which runs a process to generate simulated MRI, CT, PET or digital breast tomosynthesis (DTS) data which could be used to train and test during AI algorithm development. This simulated data could be used to generate volumetric datasets to train radiologists/medical personnel.

Some embodiments comprise a method of generating simulated volumetric datasets. To accomplish this, a 3D coordinate system is generated. A simulated 3D dataset comprising a set of voxels wherein each voxel within said set of voxels has an assigned data unit within said 3D coordinate system is generated. A discrimination process on said simulated 3D dataset wherein said discrimination process determines whether the dataset appears real or appears fake is performed. Voxel(s) within said simulated 3D dataset when discrimination process determines that said simulated 3D dataset appears fake are modified.

Some embodiments comprise wherein groups of voxels comprising subvolumes of varying anatomic and pathologic structures are inserted into the said simulated 3D dataset.

Some embodiments comprise performing analysis of a set of real medical imaging examinations to generate metrics comprises: performing segmentation of anatomic structures within the said simulated dataset; and, performing numerical analysis of said segmented anatomic structures. Additionally, numerical analysis includes mean; median; mode; standard deviation; variance; histogram type analysis; and, advanced statistical methods to characterize the data.

Some embodiments further comprise wherein the said discrimination process of said simulated 3D dataset compares metrics of said simulated 3D dataset with metrics of actual 3D datasets. Some embodiments comprise wherein said simulated data is modified under conditions wherein the metrics of said simulated data differ from the metrics of said real imaging examinations. Some embodiments comprise wherein generating a simulated 3D dataset utilizes at least one of the group comprising: inserting sub-volume approach; and, a layer-by-layer approach. Some embodiments comprise insertion of real sub-volumes from actual data into said simulated 3D dataset. Some embodiments comprise insertion of simulated 3D sub-volumes into said simulated 3D dataset. Some embodiments comprise insertion of simulated 3D sub-volumes into actual patient examinations. Some embodiments comprise performing a discrimination process on said simulated 3D dataset. Some embodiments comprise performing AI analysis of reformatted images from multiple contiguous slices. Some embodiments comprise performing AI analysis of processed images including maximum intensity projection images, volume rendering images. Some embodiments comprise generating a single anatomic structure, an age-specific normal examination, imaging artifacts, noise, a gender-specific examination, and varying pathologic conditions. Some embodiments comprise dialing a difficulty level associated with some particular pathology for testing purposes wherein said difficulty level is related to at least one of the group comprising: size of lesion; conspicuity of lesion; presence of imaging artifacts; and, frequency of disease. Some embodiments comprise performing a simulation of pathologic growth occurs over time; and, a simulation of a changing imaging feature (e.g., a pulmonary nodule grows spiculations). Some embodiments comprise using simulated volumetric datasets for a medical education at a time-step interactive process by performing the steps of: selecting the demographics of the patient; selecting the pathology; selecting the imaging; and modifying said medical imaging examination to simulate pathology. Some embodiments comprise wherein said pathology comprises one of the group comprising: tumor(s); infection(s); traumatic injury (ies); and, other known diseases. Some embodiments comprise wherein a user provides feedback to the AI process to denote the fake appearing region through use of a 3D volume cursor.

Some embodiments comprise a method of using a generative adversarial network to create a first image slice, using a generative adversarial network to create a second image slice, reconstructing a reformat from a said first slice and said second slice, and performing a discrimination process on said reformat. Some embodiments comprise varying reformats (e.g., axial, sagittal, coronal, oblique).

Some embodiments comprise wherein using an AI process to create a first image slice, using an AI process to create a second image slice, reconstructing a reformat from a said first slice and said second slice, and performing a discrimination process on said reformat. Some embodiments comprise varying reformats (e.g., axial, sagittal, coronal, oblique). Some embodiments comprise wherein a user provides feedback to the AI process to denote the fake appearing region through use of a 3D volume cursor.

Some implementations comprise a control device used by medical personnel (e.g., but not limited to a joy stick or game controller developed in accordance with USPTO patent application Ser. No. 16/524,275, A METHOD AND APPARATUS FOR USE OF GEO-REGISTERED TOOLS TO OPTIMIZE DISPLAY OF 3D MEDICAL IMAGING EXAMS, from which commands are issued to change viewing points, rotate images, etc. (described below) and augmented reality (AR)/virtual reality (VR) headset which displays the simulated 3D datasets (e.g., MRI, CT, PET, SPECT or DTS data) in true stereoscopic format. Further, some implementations will have geo-registered tools (e.g., focal point pen to annotate the simulated 3D data).

Some implementations comprise but, are not limited to, a better way to conduct the training portion of AI algorithm development. For example, a known feature (e.g., a dangerous appearing cluster of microcalcifications from a known actual patient case) can be inserted into a simulated dataset. Alternatively, a simulated cluster of microcalcifications (e.g., a dangerous appearing cluster of microcalcifications from a computer generated case) can be inserted into a simulated dataset.

Some implementations would start with only data of a specific organ. For example, radiologists typically follow a checklist (e.g., heart, lungs, liver, etc.) and go through the set of medical images in the axial plane, sagittal plane and coronal plane. During each succeeding time through the set, the radiologist would proceed through a similar checklist (e.g., heart, lungs, liver, etc.). The medical image data for each specific organ would be converted to 3D, which is taught by U.S. Pat. No. 8,384,771, METHOD AND APPARATUS FOR THREE DIMENSIONAL VIEWING OF MEDICAL IMAGES. Note: in some implementations, an arbitrarily large set data would be created by simulation such that it matched statistically the tissue types and distributions of the current organ. This data would then be filtered in accordance with U.S. patent application Ser. No. 15/904,092, PROCESSING 3D MEDICAL IMAGES TO ENHANCE VISUALIZATION, such that the tissue remaining tissue would be representative of a particular condition of concern and a corresponding set of benign conditions. For example: cancerous tumors vs. benign tumors; microcalcifications of a linear or branching pattern vs. microcalcifications in a spherical pattern or randomly dispersed. In this embodiment, only data from this particular organ type would be provided for training.

Some implementations would provide for an interactive process wherein the radiologist/medical personnel would interact with the AI algorithm process wherein the radiologist/medical personnel would annotate the tissue of concern and that tissue of non-concern to expedite the AI algorithm process. As the algorithms improved in their accuracy, simulated data could increasingly include data of tissue of non-interest.

Some implementations comprise but, are not limited to a set of testing 3D simulated data, which could be utilized to estimate AI performance in terms of accuracy of diagnosis.

Some implementations comprise but, are not limited to generation of 2D data sets of variable thickness slices that correspond to the 3D data. The training portion of AI algorithm development could be applied to the 2D data.

Some implementations comprise but, are not limited to a set of testing 2D simulated data, which could be utilized to estimate AI performance in terms of accuracy of diagnosis.

Some implementations the algorithms developed using this process would tested against algorithms available through industry and academia for diagnosis accuracy.

Some implementations comprise but, are not limited to generating simulated data of artifacts to mimic artifacts that naturally occur in the normal radiological examination process. Examples of such artifact include, but are not limited to, the following: streak artifact, motion artifact; radio-opaque objects external to the patient; noise; ghosting; aliasing; misregistration; etc.

Some implementations comprise but, are not limited to providing a better way to train radiologist/medical personnel by looking at a geo-registered simulated 3D volume(s) through creation and display of true stereoscopic images and being able to rotate, zoom, fly into this volume and/or add false color. Tissue of specific interest can be isolated and encapsulated within a 3D cursor. And, data can be filtered to showcase the tissue of concern while eliminating extraneous tissue. These techniques enable the radiologist/medical person viewing the 3D data gain a thorough understanding of the underlying structure of multiple examples of conditions listed above (and many more).

Some implementations comprise but, are not limited to providing a method for generating a simulated dataset of a specific anatomy or pathology for a specific patient. For example, a radiologist/medical professional may be in need for a normal brain CT of a seven-year-old boy so he/she can teach a more junior radiologist neuroanatomy; however, this examination may not be readily available on the hospital records system. Thus, methods described in this patent can be performed in order to generate the desired dataset. Alternatively, a radiologist/medical professional may want a MRI of the breast containing a speculated, enhancing mass representing breast cancer; however, this hospital may have only recently installed an MRI scanner and would not have such a case in their files. Therefore, the methods described in this patent can be performed in order to generate the desired dataset. Innumerable anatomies and pathologies can be simulated through the processes in this patent, which include, but are not limited to, the following: simulated MRI brain examination of a glioblastoma in an 80 year old man; simulated chest CT of pulmonary fibrosis and superimposed pneumonia in a 60 year old woman; simulated CT scan of a scaphoid fracture in a 10-year boy, etc. Additionally, other types of voxelated datasets can be generated, which includes, but is not limited to the following: LiDAR; radar; and, sonar datasets.

To accomplish this method, an apparatus should comprise the following items. First, a computer (or interface to cloud computing) which applies software to generate simulated MRI, CT, PET, SPECT or DTS medical images of body tissues at the direction of medical personnel. Second, a head display unit (or other type display which provides true stereoscopic imagery) that presents the geo-registered 3D MRI, CT, PET or DTS medical image(s). Third, a geo-registered focal point pen that interacts with geo-registered 3D MRI, CT, PET or DTS medical images. Fourth, a geo-registered pedestal/platform that interacts with geo-registered 3D MRI, CT, PET or DTS medical images. Fifth, a geo-registration master control platform component interacts with other components and, in conjunction with geo-processing software would enable geo-registration of these components within the overall system containing the volumetric MRI, CT, PET or DTS medical images, and other system components. Sixth, software for geo-registration of components within the system and generation of images to be displayed on the head display unit.

The next embodiment of this patent comprise but, is not limited to a method to generate multiple sets of simulated 3-Dimension data of MRI, CT, PET or DTS medical images. This would in accordance with several steps. First, a 3-dimension scale with voxels whose size corresponds to the contrast resolution and spatial resolution of MRI, CT, PET or DTS medical images. The volumetric size of the simulated tissue (e.g., organ within the body) would be the same size of the corresponding patient tissue and the total number of voxels would be equal to the total number of pixels in the 2-dimension slices of MRI, CT, PET or DTS. Second, a 3-dimension volume with voxels whose gray scales (e.g., −2,000 to +2,000 for CT) which correspond to those gray scales of MRI, CT, PET or DTS medical images. Third, a 3-dimension volume would be populated (for example, but not limited to, filled sequentially by nested do loops corresponding to the X, Y, Z coordinate scheme) with voxels whose gray scales are typical of those associated with tissue being simulated. This process can be replicated an arbitrarily large number of times. Fourth, a gray scales of conditions being simulated (e.g., cancerous or benign tumors) can be substituted for the normal/typical tissue being simulated. Fifth, the size, shape, location and orientation of conditions being simulated (above) can be changed in accordance with selected random distributions. This process can be replicated an arbitrarily large number of times. Sixth, the size, shape, location and orientation of conditions being simulated (per 2d, above) can be changed (e.g., to reflect progression of disease or treatment thereof). Seventh, the sets of 3D medical image data can be separated into training data for AI algorithm development and testing data for estimating AI algorithm performance. Eighth, the sets of 3D medical image data can be used as training data for radiologists or other medical personnel.

The next embodiment of this patent comprises but, is not limited to, a process for development of AI algorithms to perform diagnosis of medical images. This process would involve the multiple steps. Take a large number of MRI, CT, PET or DTS medical images (individually by type of imaging technology) and convert them from 2D slices to a 3D volume. (USPTO U.S. Pat. No. 8,384,771, METHOD AND APPARATUS FOR THREE DIMENSIONAL VIEWING OF IMAGES). Perform segmentation in accordance with radiologist checklist (e.g., organs (heart, liver, etc.) mussel skeletal, brain, etc.) in accordance with U.S. patent application Ser. No. 15/904,092, PROCESSING 3D MEDICAL IMAGES TO ENHANCE VISUALIZATION. For each of the segmented items in 3b, above, perform a statistical analysis of distribution of density units (e.g., Hounsfield for CT) within tissue types and among tissue types across the images collected in Claim 3a, above, by medical imaging technology (MRI, CT, PET or DTS). For each of the items above and using the statistical distributions, above generate an arbitrarily large data set of simulated 3D medical images. Divide these image sets into a training set and a testing set. For these 3D simulated images within the training data sets, perform filtration such that only tissue of concern and similar tissue which is not of concern remains. (USPTO patent application Ser. No. 15/904,092, PROCESSING 3D MEDICAL IMAGES TO ENHANCE VISUALIZATION). Train AI algorithms on the 3D simulated tissue obtained, above. Introduce tissue which is not of concern into the 3D simulated images. Re-fine training of AI algorithms, above using 3D simulated images, above. Apply the resultant AI algorithms from Claim 3h, above to the testing set of images from Claim 3d. Record diagnostic accuracy. As an option, have radiologist/medical personnel identify identifying features using the geo-registered pen to annotate these features in a representative sample of the images, above. Integrate the information gleaned from the annotations into the AI algorithm development.

The next embodiment of this patent comprises use of head mounted displays to provide radiologists or other medical personnel with true stereoscopic 3D images of simulated 3D MRI, CT, PET, SPECT or DTS medical images using the plotting and display processes contained in USPTO U.S. Pat. No. 8,384,771, METHOD AND APPARATUS FOR THREE DIMENSIONAL VIEWING OF IMAGES USPTO U.S. Pat. No. 9,349,183, METHOD AND APPARATUS FOR THREE DIMENSIONAL VIEWING OF IMAGES, and USPTO U.S. Pat. No. 9,473,766, METHOD AND APPARATUS FOR THREE DIMENSIONAL VIEWING OF IMAGES, in connection with the 3D simulated data sets generated, above. Features at the control of the radiologist/medical personnel would include: rotating, zooming, changing view points, and flying thru the 3D volume; adding false color to certain tissue types; changing transparency of certain tissue types; Using convergence to better focus on tissue of interest; using of alternative types of displays.

The next embodiment of this patent comprises use of the volume-subtending, interactive 3D cursor (USPTO U.S. Pat. No. 9,980,691, METHOD AND APPARATUS FOR THREE DIMENSIONAL VIEWING OF IMAGES) in connection with the 3D simulated data sets generated, above. Features at the control of the radiologist/medical personnel would include: moving the 3D cursor, at the control of the radiologist, to a desired location within the 3D volume being simulated; rotation, zooming, and re-sizing of the 3D cursor; adding false color to contents of the 3D cursor; performing a count of voxels within the 3D cursor; performing statistics on the type of voxels within the cursor (e.g., provide histogram of numbers of voxels by tissue type; eliminating all tissue external to the cursor; eliminating specified tissue types within the 3D cursor; use the 3D cursor in conjunction with an AI algorithm (e.g., place 3D cursor over the concerning tissue and labeling the tissue to train the AI algorithm).

The next embodiment of this patent comprises use of segmentation (i.e., determining the boundary of body organs) (USPTO patent application Ser. No. 15/904,092, PROCESSING 3D MEDICAL IMAGES TO ENHANCE VISUALIZATION) in connection with the 3D simulated data sets generated, above. This feature would be invoked under the control of the radiologist/medical personnel.

The next embodiment of this patent comprises use of filtering (e.g., eliminating certain tissue types) (USPTO patent application Ser. No. 15/904,092, PROCESSING 3D MEDICAL IMAGES TO ENHANCE VISUALIZATION) in connection with the 3D simulated data sets generated, above. This feature would be invoked under the control of the radiologist/medical personnel.

The next embodiment of this patent comprises manipulation of voxels (i.e., voxel addition, voxel elimination or voxel manipulation of voxel size, shape, location, orientation, or internal property) (USPTO Patent Application 62/695,868, INTERACTIVE VOXEL MANIPULATION STRATEGIES IN VOLUMETRIC MEDICAL IMAGING ENABLES VIRTUAL MOTION, DEFORMABLE TISSUE, AND VIRTUAL RADIOLOGICAL DISSECTION) in connection with the 3D simulated data sets generated, above. This feature would be invoked under the control of the radiologist/medical personnel.

The next embodiment of this patent comprises use of a geo-registered tools (e.g., using a geo-registered pen to enable the radiologist/medical personnel to point out certain distinguishing features to assist in training AI algorithms or training the radiologist/medical personnel) (USPTO Patent Application 62/711,658, A METHOD AND APPARATUS FOR USE OF GEO-REGISTERED TOOLS TO OPTIMIZE DISPLAY OF 3D MEDICAL IMAGING EXAMS) in connection with the 3D simulated data sets generated, above. This feature would be invoked under the control of the radiologist/medical personnel.

The next embodiment of this patent comprises use of the AI process (e.g., enabling the radiologist/medical personnel to adjudicate differences in diagnoses between radiologist/medical personnel and AI algorithms (USPTO Patent Application 62/651,934, A METHOD AND APPARATUS FOR THE INTERACTION OF VIRTUAL TOOLS AND GEO-REGISTERED TOOLS: VIDEO GAMES) in connection with the 3D simulated data sets generated. This feature would be invoked under the control of the radiologist/medical personnel.

The next embodiment of this patent is software which will implement the following: simulation of MRI, CT, PET or DTS medical image data through establishing a 3D grid system and associated X, Y, Z coordinate system; a mathematical process to populate a 3D volume with simulated data corresponding to and representative of MRI, CT, PET or DTS medical images; potting and displaying the simulated 3D MRI, CT, PET or DTS data; establishing the 3D cursor with associated functionality; establishing the process by which the 3D volume of simulated data can be segmented; establishing the process by which the 3D volume of simulated data can be filtered; establishing the process by which voxels within the 3D volume of simulated data can be manipulated; establishing the geo-registered tools with associated functionality; establishing the adjudication process for times when radiologists/medical personnel diagnoses conflict with AI algorithm diagnoses; and, implementing the overall system functionality.

BRIEF DESCRIPTION OF THE FIGURES

FIG. 9 provides a flow diagram and illustration for using the 3D cursor in conjunction with radiologist-assisted machine learning.

FIG. 15 illustrates an example radiology report incorporating the 3D cursor and radiologist-assisted machine learning reporting technique.

FIG. 21 illustrates a flow chart of generating a simulated realistic 3D radiological dataset.

FIG. 28 illustrates a lobule of fat generated through artificial intelligence.

DETAILED DESCRIPTION

Some aspects, features and implementations described herein may include machines such as computers, electronic components, optical components, and processes such as computer-implemented steps. It will be apparent to those of ordinary skill in the art that the computer-implemented steps may be stored as computer-executable instructions on a non-transitory computer-readable medium. Furthermore, it will be understood by those of ordinary skill in the art that the computer-executable instructions may be executed on a variety of tangible processor devices. For ease of exposition, not every step, device or component that may be part of a computer or data storage system is described herein. Those of ordinary skill in the art will recognize such steps, devices and components in view of the teachings of the present disclosure and the knowledge generally available to those of ordinary skill in the art. The corresponding machines and processes are therefore enabled and within the scope of the disclosure.

The terminology used in this disclosure is intended to be interpreted broadly within the limits of subject matter eligibility. The terms "logical" and "virtual" are used to refer to features that are abstractions of other features, e.g. and without limitation abstractions of tangible features. The term "physical" is used to refer to tangible features. For example, multiple virtual computing devices could operate simultaneously on one physical computing device. The term "logic" is used to refer to special purpose physical circuit elements and software instructions that are stored on a non-transitory computer-readable medium and implemented by multi-purpose tangible processors. Furthermore, the terminology "3D cursor" is meant to refer to a type of cursor that subtends a volume. The terminology "sub-volume" may be used to in conjunction with 3D cursor to indicate that the volume within the 3D cursor represents only a fraction of the volume in the entire medical image (e.g., liver is contained in a 3D cursor, or sub-volume, of the entire abdomen and pelvis CT scan imaging volume).

U.S. Provisional Patent Application 62/748,555 titled A METHOD AND APPARATUS FOR RADIOLOGIST ASSISTED MACHINE LEARNING, filed Oct. 22, 2018 is incorporated by reference. U.S. Provisional Patent Application 62/651,934 titled A METHOD TO OPTIMIZE THE INTERACTION BETWEEN A RADIOLOGIST AND ARTIFICIAL INTELLIGENCE COMPUTER SYSTEM THROUGH INTERACTIVE, VOLUME-SUBTENDING 3D CURSOR USE TO IMPROVE DIAGNOSTIC ACCURACY, filed Apr. 3, 2018 is incorporated by reference.

Figure 1:
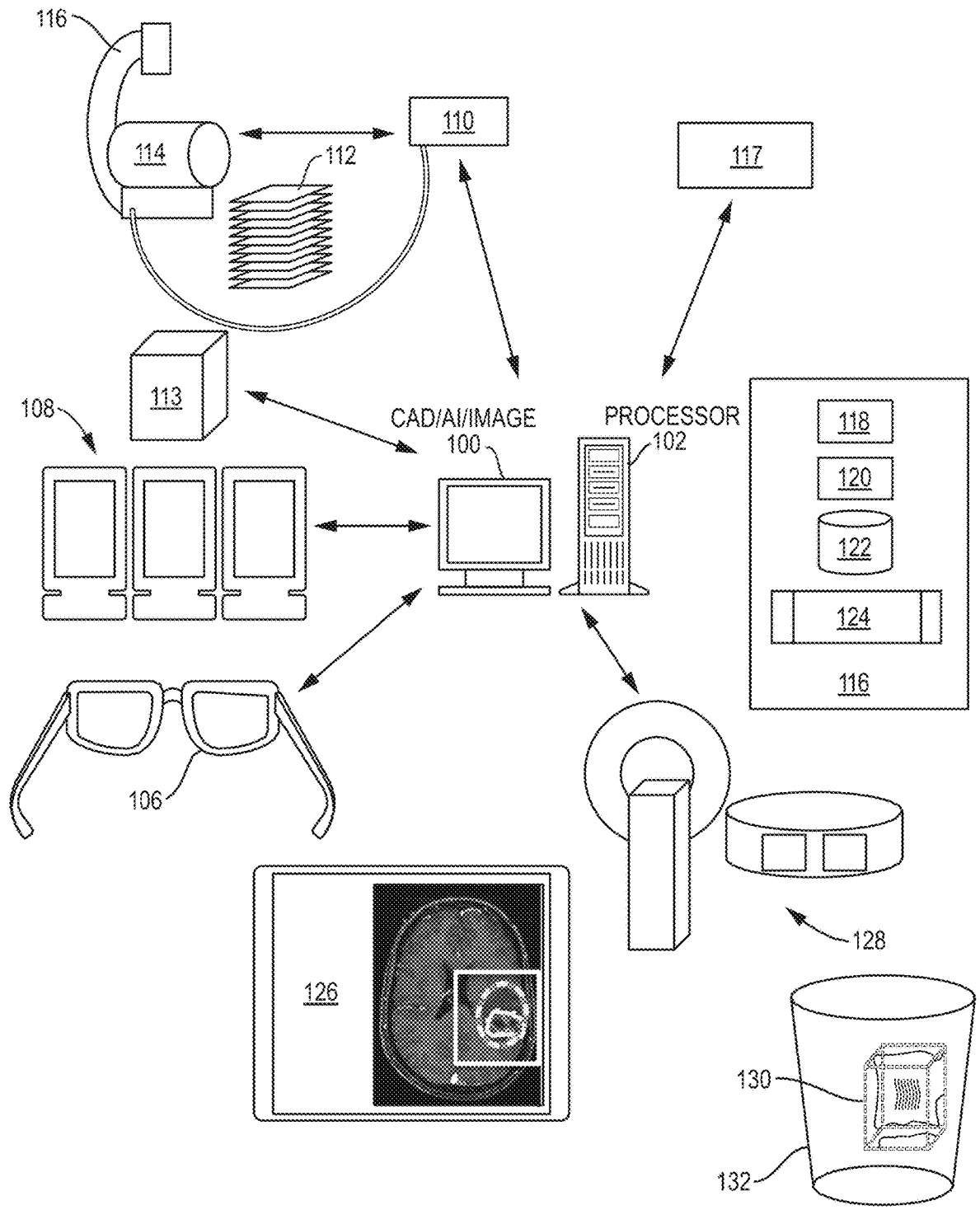
FIG. 1 illustrates the key components for an integrated radiologist-assisted machine learning process.

FIG. 1 illustrates an imaging and diagnostic system associated with radiologist-assisted machine learning capabilities. In general, machine learning enables a computer to progressively improve performance of a task without being explicitly programmed to perform every aspect of that task. CAD and/or AI programs 100 running on an image processing and diagnostic computer 102 partially automate medical diagnostics and learn from radiologist review. The system includes external devices such as a controller 104 and a headset 106. An IO device 108 includes a viewing station with multiple 2D monitors. Communications linkages may include a link between any of the above elements, such as a link between the controller and the image processing and diagnostic computer, a link between the image processing and diagnostic computer and the headset; and a links between the image processing and diagnostic computer, a Picture Archiving Communications System (PACS) system 110 which can display cross-sectional images 112. Images can be processed to form a 3D volume 113 in accordance with USPTO U.S. Pat. No. 8,384,771. Patient medical records 117 can also be displayed on the monitors. Also running as programs on the image processing and diagnostic computer 116 are an image processing system as disclosed in U.S. patent application Ser. No. 15/904,092 for PROCESSING 3D MEDICAL IMAGES TO ENHANCE VISUALIZATION, filed Feb. 23, 2018, which is incorporated by reference, for 3D image generation and image manipulation based on commands from the controller, a report generator, and AI for data extraction from PACS and patient's medical records, which may include responses to a questionnaire. The 2D medical images 112 of an anatomic structure 114 of interest are generated. Imaging capabilities 116 may include x-ray, ultrasound, mammogram, computed tomography, magnetic resonance imaging, positron emission tomography, single photon emission computed tomography, or tomosynthesis, for example and without limitation. The 2D medical images 112 are provided to the image processing and diagnostic computer 100, that includes processors 118 (e.g., CPUs and GPUs), volatile memory 120 (e.g., RAM), and non-volatile storage 122 (e.g. HDDs and SSDs). A program 124 running on the image processor implements one or more of the steps described in this patent to accomplish radiologist-assisted machine learning (RAML). The medical images are displayed on an IO device 126 and marked up by the radiologist. The IO device may include a virtual or augmented reality headset 106, monitor, tablet computer, PDA (personal digital assistant), mobile phone, or any of a wide variety of devices, either alone or in combination. The IO device may include a touchscreen and may accept input from external devices (represented by 128) such as a keyboard, mouse, and any of a wide variety of equipment for receiving various inputs. Finally, a series of virtual objects including interactive volume-subtending 3D cursors 130 and virtual buckets 132 will also be integral to this system.

Figure 2:
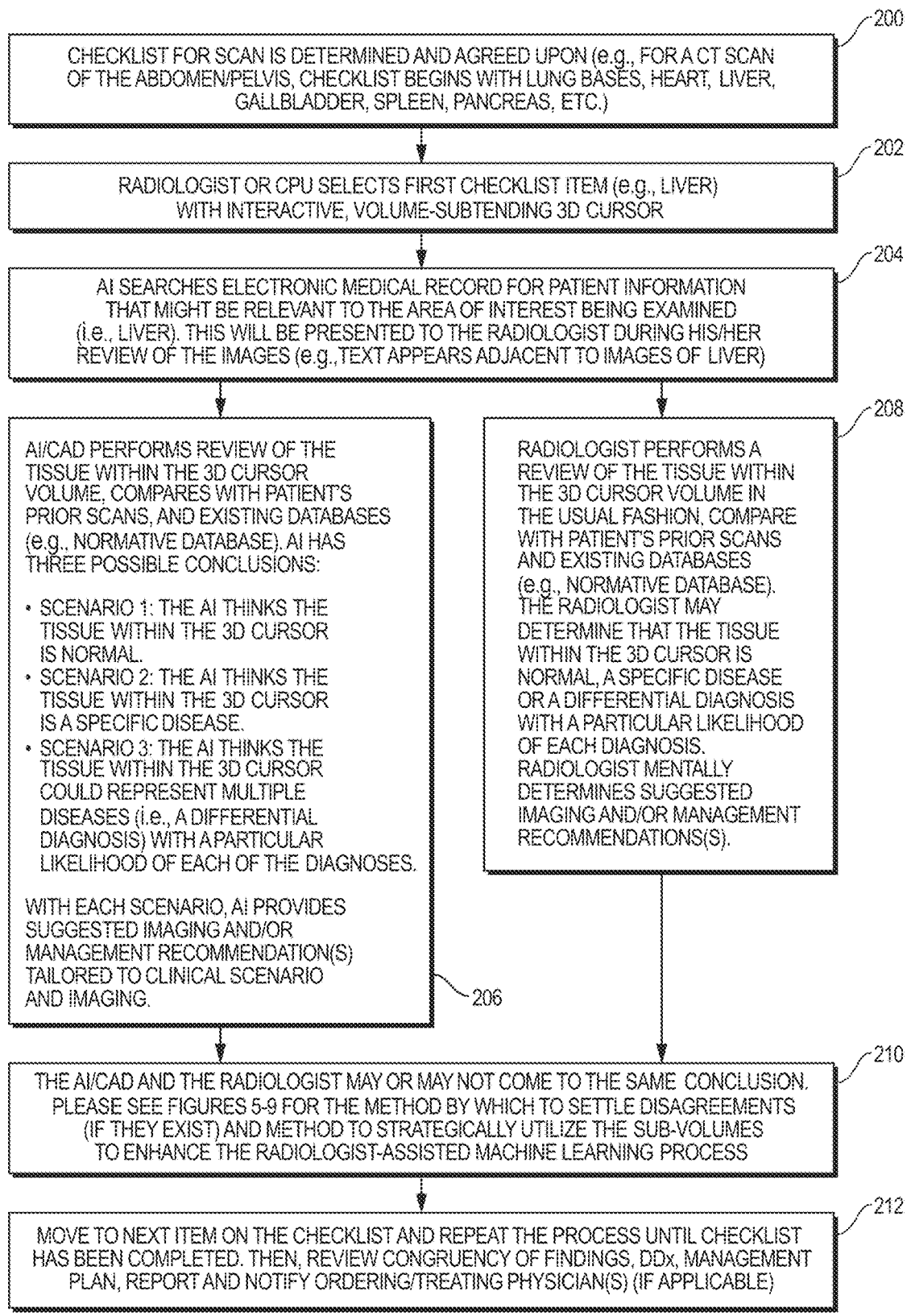
FIG. 2 is a generalized flow diagram that illustrates a checklist-based volume-by-volume 3D cursor approach for radiologist-assisted machine learning.

FIG. 2 is a generalized flow diagram that illustrates a checklist-based volume-by-volume 3D cursor approach for radiologist-assisted machine learning. Preparatory steps may include downloading cases for review from a PACS and creating a 3D volume from a set of 2D image slices as outlined in USPTO U.S. Pat. No. 8,384,771. An additional preparatory step may include performing segmentation of the imaged tissues into discrete tissue types. As indicated in step 200, the radiologist (or other physician) follows a checklist of key body parts which are reviewed in a sequential fashion. For example, for a CT scan of the abdomen/pelvis, the checklist may include lung bases, heart, liver, gallbladder, spleen, pancreas, etc. As indicated in step 202, the radiologist or CPU selects first checklist item (e.g., liver) with interactive, volume-subtending 3D cursor. As indicated in step 204, the AI searches electronic medical record for patient information that might be relevant to the area of interest being examined (i.e., liver). This will be presented to the radiologist during his/her review of the images (e.g., text appears adjacent to images of liver). For example, important information may include the most recent liver function tests during the review of the liver. As indicated in step 206, the volume within the 3D cursor is analyzed by the AI and/or CAD algorithm. The algorithm compares with the patient's prior scans and existing databases. AI has three possible conclusions. First, AI may determine that the tissue within the 3D cursor is normal. Second, the AI may determine that the tissue within the 3D cursor is a specific disease. Third, the AI may determine that the tissue within the 3D cursor could represent multiple diseases (i.e., a differential diagnosis) with a particular likelihood of each of the diagnoses. With each scenario, AI provides suggested imaging and/or management recommendation(s) tailored to clinical scenario and imaging. In a concurrent fashion, the radiologist performs a review 208 of the tissue within the 3D cursor volume in this usual fashion or using advanced visualization techniques. He/she will compare with the patient's prior scans and existing databases as well. The radiologist may determine that the tissue within the 3D cursor is normal, a specific disease or a differential diagnosis with a particular likelihood of each diagnosis. The radiologist mentally determines suggested imaging and/or management recommendation(s). As indicated in step 210, the AI/CAD and the radiologist may or may not come to the same conclusion. Please see FIGS. 3-7 for the method by which to settle disagreements (if they exist) and method to strategically utilize the sub-volumes to enhance the radiologist-assisted machine learning process. As indicated in step 212, the radiologist will move to next item on the checklist and repeat the process until checklist has been completed. Then, review congruency of findings, DDx, management plan, report and notify ordering/treating physician(s) (if applicable).

Figure 3:
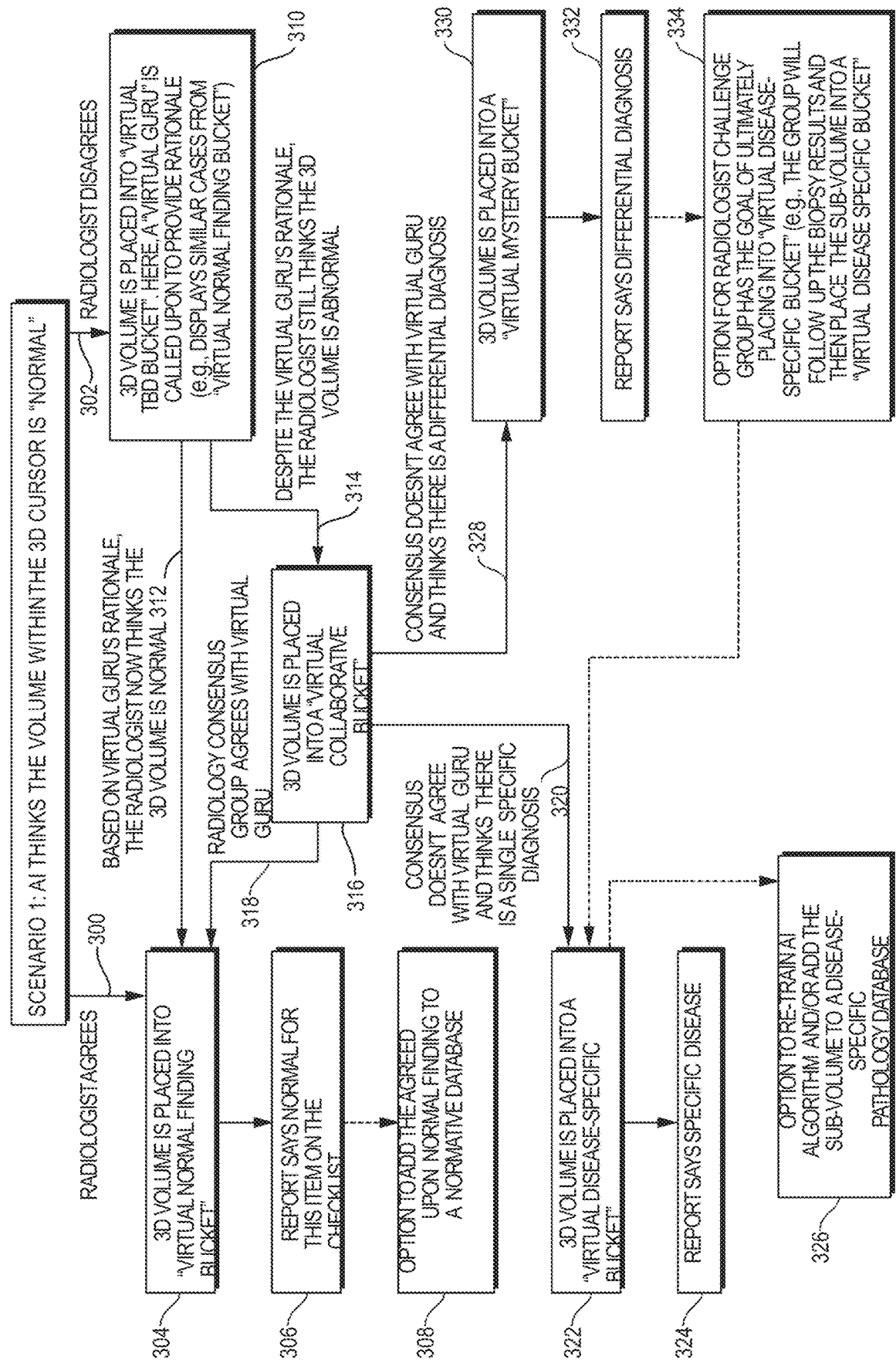
FIG. 3 illustrates a flow diagram for radiologist-assisted machine learning for the scenario wherein the AI concludes that the volume within the 3D cursor is "normal".

FIG. 3 illustrates a flow diagram for radiologist-assisted machine learning for the scenario wherein the AI concludes that the volume within the 3D cursor is "normal". As indicated in 300, the radiologist may agree with the AI's conclusion that the volume within the 3D cursor is normal. If the radiologist agrees, the 3D volume can be placed into a "virtual normal finding bucket" 304. The radiology report will state that this item on the checklist is normal 306. The radiologist has the option to add the agreed upon normal finding to a normative database 308. However, the radiologist may also disagree with the AI 302. In this case, the 3D volume is placed into "virtual TBD bucket" 310. Here, a "virtual guru" is called upon to provide rationale (e.g., displays similar cases from virtual normal finding bucket"). If, based on the virtual guru's rationale, the radiologist now thinks the volume within the 3D cursor is normal 312, the radiologist places the 3D volume into a "virtual normal finding bucket" 304. If despite the virtual guru's explanation, the radiologist still thinks the volume within the 3D cursor is abnormal 314, he/she places the volume within the 3D cursor into a "virtual collaborative bucket" 316. At this juncture, the interpreting radiologist collaborates with other radiologist to evaluate the suspected abnormality within 3D cursor. This could be in the form of a formal radiology conference or informal "curbside" radiologist-to-radiologist consult. If the radiology consensus agrees with the virtual guru that the volume within the 3D cursor is normal 318, the volume is placed into the "virtual normal finding bucket" 304. If the radiology consensus doesn't agree with the virtual guru and believes that there is a single specific diagnosis 320, then the 3D volume is placed into a "virtual disease-specific bucket" 322. Then, the report will discuss the specific disease (or pathology entity) 324. Additional options include retraining the AI algorithm and/or adding the 3D volume to a disease specific pathology database 326. If the radiology consensus doesn't agree with the virtual guru and thinks that instead of the volume within the 3D cursor being normal, there is an abnormality with a differential diagnosis 328. The 3D volume is placed into a "virtual mystery bucket" 330. The report states the differential diagnosis with the specified order as determined by the radiologist and radiologist's consensus group 332. Then, there is an option for the radiologist challenge group with the goal of ultimately placing the 3D volume into a "virtual disease specific bucket" 334. For example, the group will follow up the biopsy results and then place the sub-volume into a "virtual disease specific bucket" 322.

Figure 4:
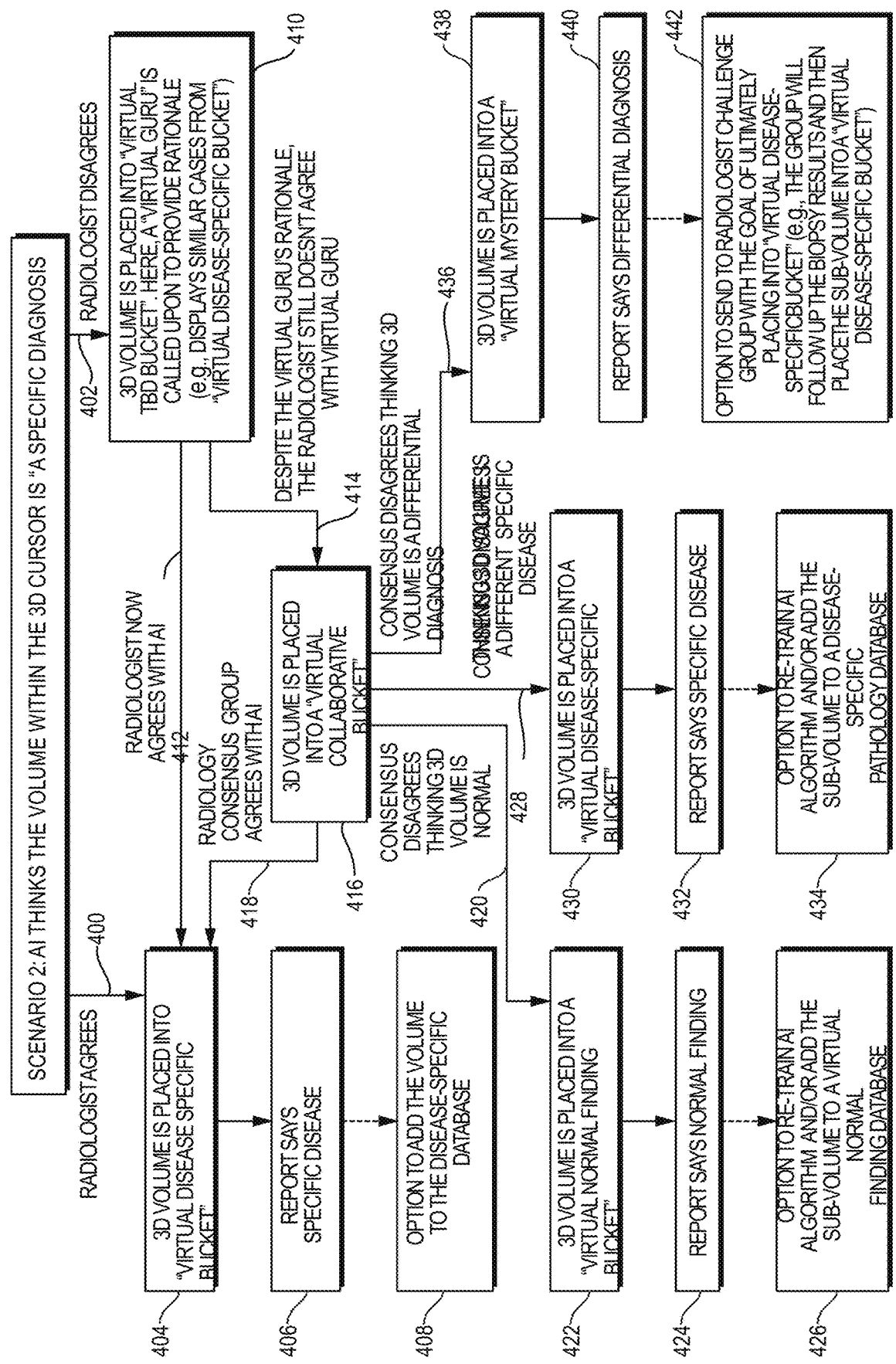
FIG. 4 illustrates a flow diagram for radiologist-assisted machine learning for the scenario wherein the AI concludes that the volume within the 3D cursor is a "specific diagnosis".

FIG. 4 illustrates a flow diagram for radiologist-assisted machine learning for the scenario wherein the AI concludes that the volume within the 3D cursor is a "specific disease". As indicated in 400, the radiologist may agree with the AI's conclusion that the volume within the 3D cursor is the said specific disease. If the radiologist agrees, the 3D volume can be placed into a "virtual disease specific bucket" 404. The radiology report will describe the specific disease 406. Please note that AI processes should also have the ability to accurately describe the both normal anatomy and pathology. Feedbacks similar to those designed in this patent through the use of 3D cursors and "virtual buckets" can also be used to improve descriptions performed by AI. The radiologist has the option to add the agreed upon 3D volume to a disease specific database 408. However, the radiologist may also disagree with the AI 402. In this case, the 3D volume is placed into "virtual TBD bucket" 410. Here, a "virtual guru" is called upon to provide rationale (e.g., displays similar cases from virtual disease specific bucket"). If, based on the virtual guru's rationale, the radiologist now thinks the volume within the 3D cursor represents the said specific disease 412, the radiologist places the 3D volume into a "virtual disease specific bucket" 404. If despite the virtual guru's explanation, the radiologist still doesn't agree with the virtual guru 414, he/she places the volume within the 3D cursor into a "virtual collaborative bucket" 416. At this juncture, the interpreting radiologist collaborates with other radiologist to evaluate the 3D volume. This could be in the form of a formal radiology conference or informal "curbside" radiologist-to-radiologist consult. If the radiology consensus agrees with the virtual guru that the volume within the 3D cursor is the said specific disease 418, the volume is placed into the "virtual disease specific bucket" 404. If the radiology consensus doesn't agree with the virtual guru and believes that the 3D volume is normal 420, then the 3D volume is placed into a "virtual normal finding bucket" 422. Then, the report will state that that item on the checklist is normal 424. Options include re-training the AI algorithm and/or adding the sub-volume to a "virtual normal finding bucket" 426. If the radiology consensus doesn't agree with the virtual guru and believes that the 3D volume is a specific disease 428, then the 3D volume is placed into a "virtual specific disease bucket" 430. Then, the report will state the specific disease 432. Options include re-training the AI algorithm and/or adding the 3D cursor volume to a disease specific pathology database 434. Finally, the radiology consensus group may disagree with the virtual guru and believe that the volume within the 3D cursor could be a differential diagnosis. In this case, the 3D volume is placed into a "virtual mystery bucket" 438. The report states the differential diagnosis with the likelihood of each diagnosis discussed 440. Options include sending the 3D cursor to a radiology challenge group with the goal of ultimately placing into "virtual disease-specific bucket" (e.g., the group will follow up the biopsy results and then place the sub-volume into a "virtual disease specific bucket" 430). Options include sending both the sub-volume of diagnostic question and the total imaging volume to the radiology challenge group.

Figure 5:
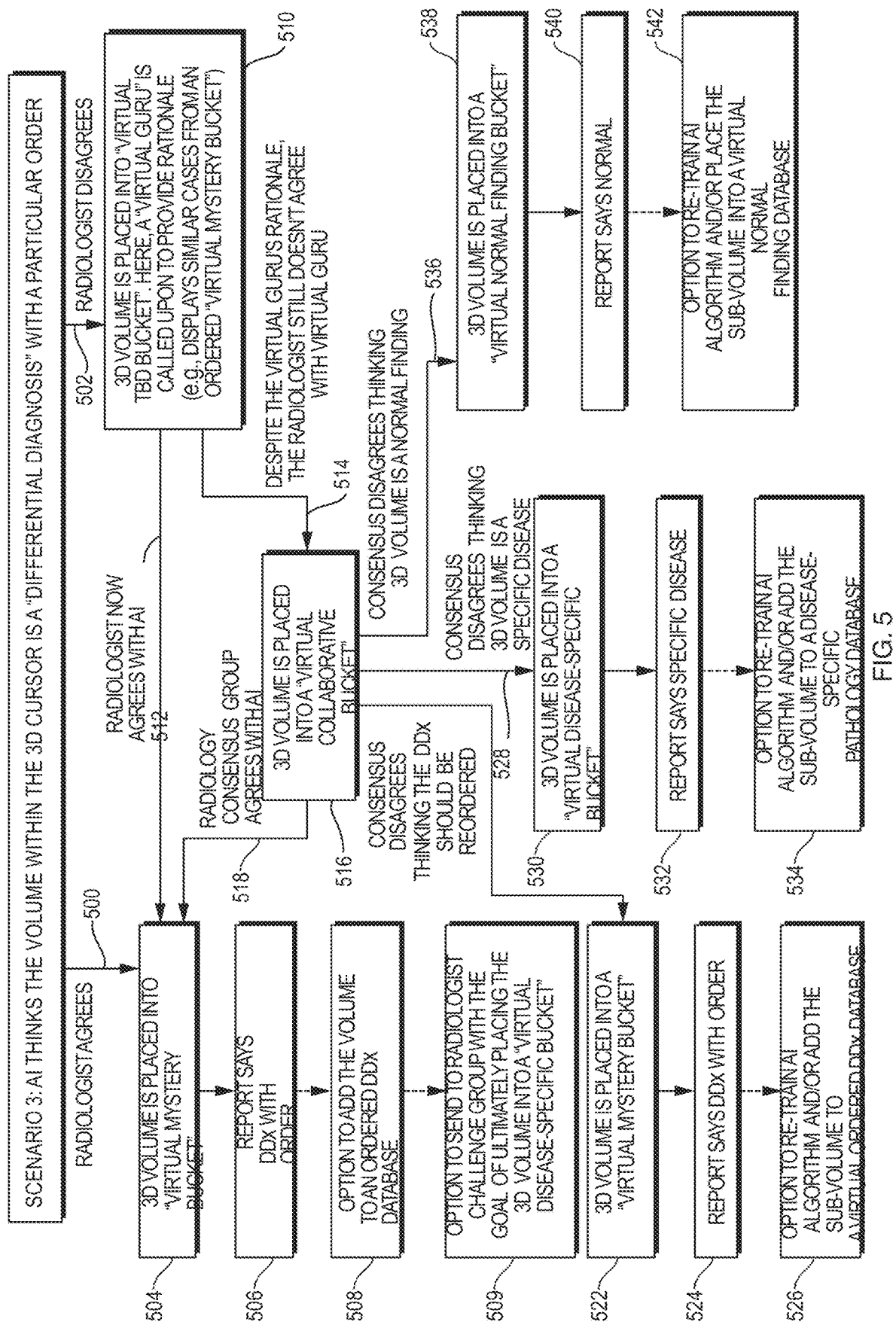
FIG. 5 illustrates a flow diagram for radiologist-assisted machine learning for the scenario wherein the AI concludes that the volume within the 3D cursor is a "differential diagnosis" with a likelihood of each diagnosis.

FIG. 5 illustrates a flow diagram for radiologist-assisted machine learning for the scenario wherein the AI concludes that the volume within the 3D cursor is a "differential diagnosis of multiple possible diseases" with a particular likelihood of each disease. As indicated in 500, the radiologist may agree with the AI's conclusion that the volume within the 3D cursor is the said differential diagnosis. If the radiologist agrees, the 3D volume can be placed into a "virtual mystery bucket" 504. The radiology report will describe the differential diagnosis 506 with the particular order. Please note that AI processes should also have the ability to accurately describe the imaging findings both normal anatomy and pathology. Furthermore, the AI system should be able to use imaging terminology as to why one differential diagnosis is favored over another differential diagnosis. Feedbacks similar to those designed in this patent through the use of 3D cursors and "virtual buckets" can also be used to improve descriptions performed by AI. The radiologist has the option to add the agreed upon 3D volume to a differential diagnosis (DDx) database 508. An additional option is to send the sub-volume in question with or without the total imaging volume to a radiologist challenge group wherein the challenge group has the goal of ultimately placing the 3D volume into a "virtual disease specific bucket." However, the radiologist may also disagree with the AI 502. In this case, the 3D volume is placed into "virtual TBD bucket" 510. Here, a "virtual guru" is called upon to provide rationale (e.g., displays similar cases from "virtual mystery bucket"). If, based on the virtual guru's rationale, the radiologist now thinks the volume within the 3D cursor represents the said differential diagnosis including the order of the differential diagnosis 512, the radiologist places the 3D volume into a "virtual mystery bucket" 504. If despite the virtual guru's explanation, the radiologist still doesn't agree with the virtual guru 514, he/she places the volume within the 3D cursor into a "virtual collaborative bucket" 516. At this juncture, the interpreting radiologist collaborates with other radiologist to evaluate the 3D volume. This could be in the form of a formal radiology conference or informal "curbside" radiologist-to-radiologist consult. If the radiology consensus group agrees with the virtual guru that the volume within the 3D cursor is the said differential diagnosis with the agreed likelihood of the differential diagnoses 518, the volume is placed into the "virtual mystery bucket" 504. The radiology consensus group may also disagree with the virtual guru and believe that the volume within the 3D cursor could be a differential diagnosis (different order, different set of diagnoses or combination thereof). In this case, the 3D volume is placed into a different "virtual mystery bucket" 522. The report states the differential diagnosis with the likelihood of each diagnosis discussed 524. An option 526 is to re-train the AI algorithm, add the 3D cursor to a differential diagnosis database and/or send the sub-volume (with or without the entire imaging volume and clinical data elements to a radiology challenge group with the goal of ultimately placing into "virtual disease-specific bucket" (e.g., the group will follow up the biopsy results and then place the sub-volume into a "virtual disease specific bucket" 530). Options include sending both the sub-volume of diagnostic question and the total imaging volume to the radiology challenge group. Finally, if the radiology consensus doesn't agree with the virtual guru and believes that the 3D volume is normal 536, then the 3D volume is placed into a "virtual normal finding bucket" 538. Then, the report will state that that item on the checklist is normal 540. Options include re-training the AI algorithm and/or adding the sub-volume to a virtual normal finding database 542.

Figure 6:
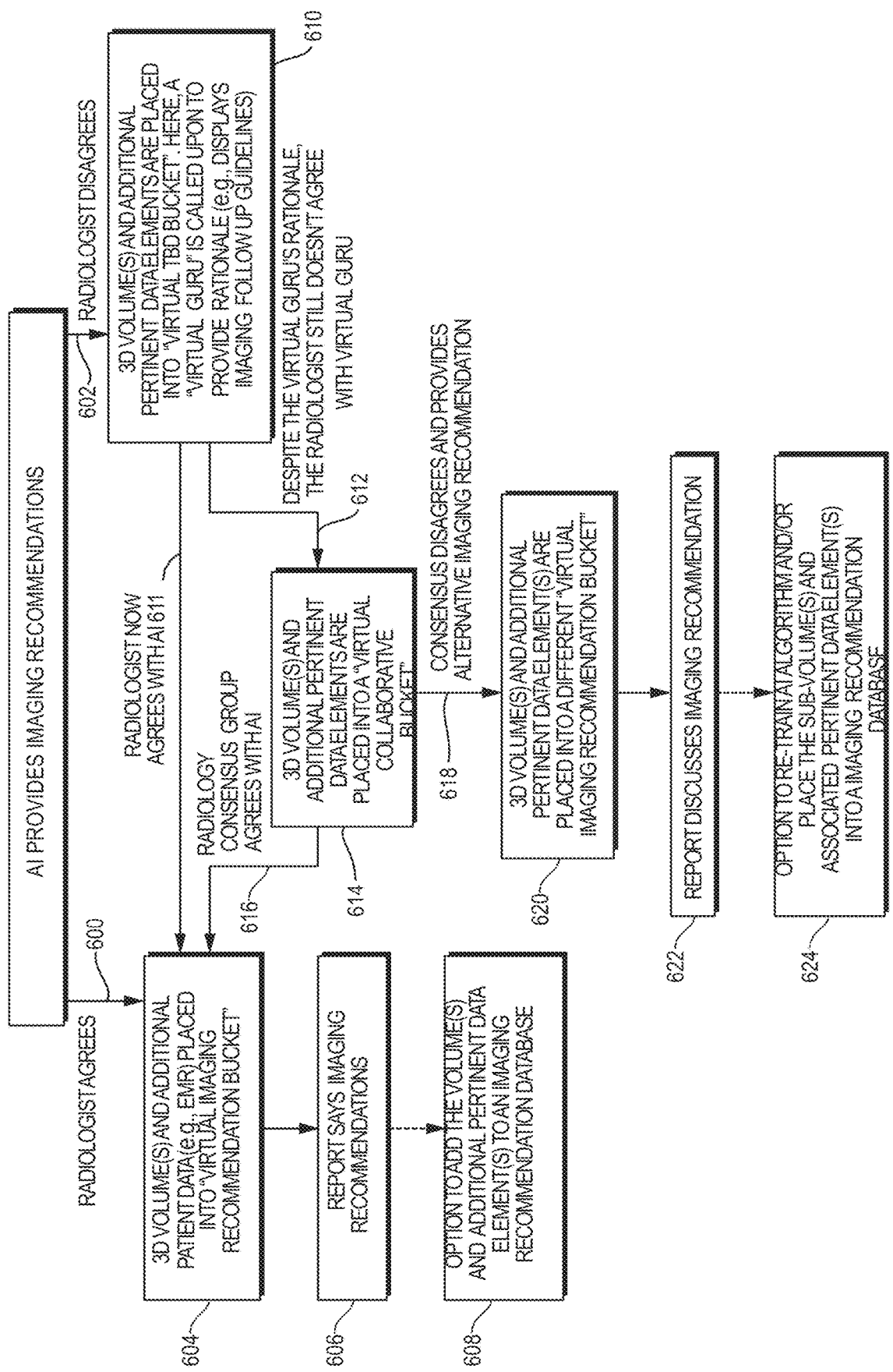
FIG. 6 illustrates a flow diagram for radiologist-assisted machine learning for the scenario wherein the AI reviews the examination and provides further imaging recommendations.

FIG. 6 illustrates a flow diagram for radiologist-assisted machine learning for the scenario wherein the AI reviews the examination and provides further imaging recommendations. If the radiologist agrees with the AI 600, then the 3D volume(s) and additional pertinent data (e.g., data from the Electronic Medical Record (EMR)) are together placed into the "virtual imaging recommendation bucket" 604. The radiology report states the imaging recommendation 606. Then, an option is to add the volume and additional pertinent data element(s) to an imaging recommendation database 608. If the radiologist disagrees with the AI 602, then the 3D volume(s) and additional pertinent data elements are placed into "virtual TBD (To Be Determined) bucket" 610. Here, a "virtual guru" is called upon to provide rationale (e.g., displays imaging follow up guidelines). If the radiologist now agrees with the AI 611, then the 3D volume(s) and additional pertinent data element(s) are added to the "virtual imaging recommendation bucket" 604. If, despite the virtual guru's rationale, the radiologist still doesn't agree with the virtual guru 612, then the 3D volume(s) and additional pertinent data element(s) are placed into a "virtual collaborative bucket" 614. If the radiology consensus group agrees with the AI 616, then the 3D volume(s) and additional pertinent data element(s) are added to the virtual imaging recommendation bucket" 604. If the radiology consensus group disagrees and believes an alternative imaging recommendation is warranted 618, then the 3D volume(s) and additional pertinent data element(s) are placed into a different "virtual imaging recommendation bucket" 620. Then, the radiology report discusses the imaging recommendations 622. An option at this juncture is to re-train the AI algorithm and/or place the sub-volume(s) and associated pertinent data element(s) into a imaging recommendation database 624.

Figure 7:
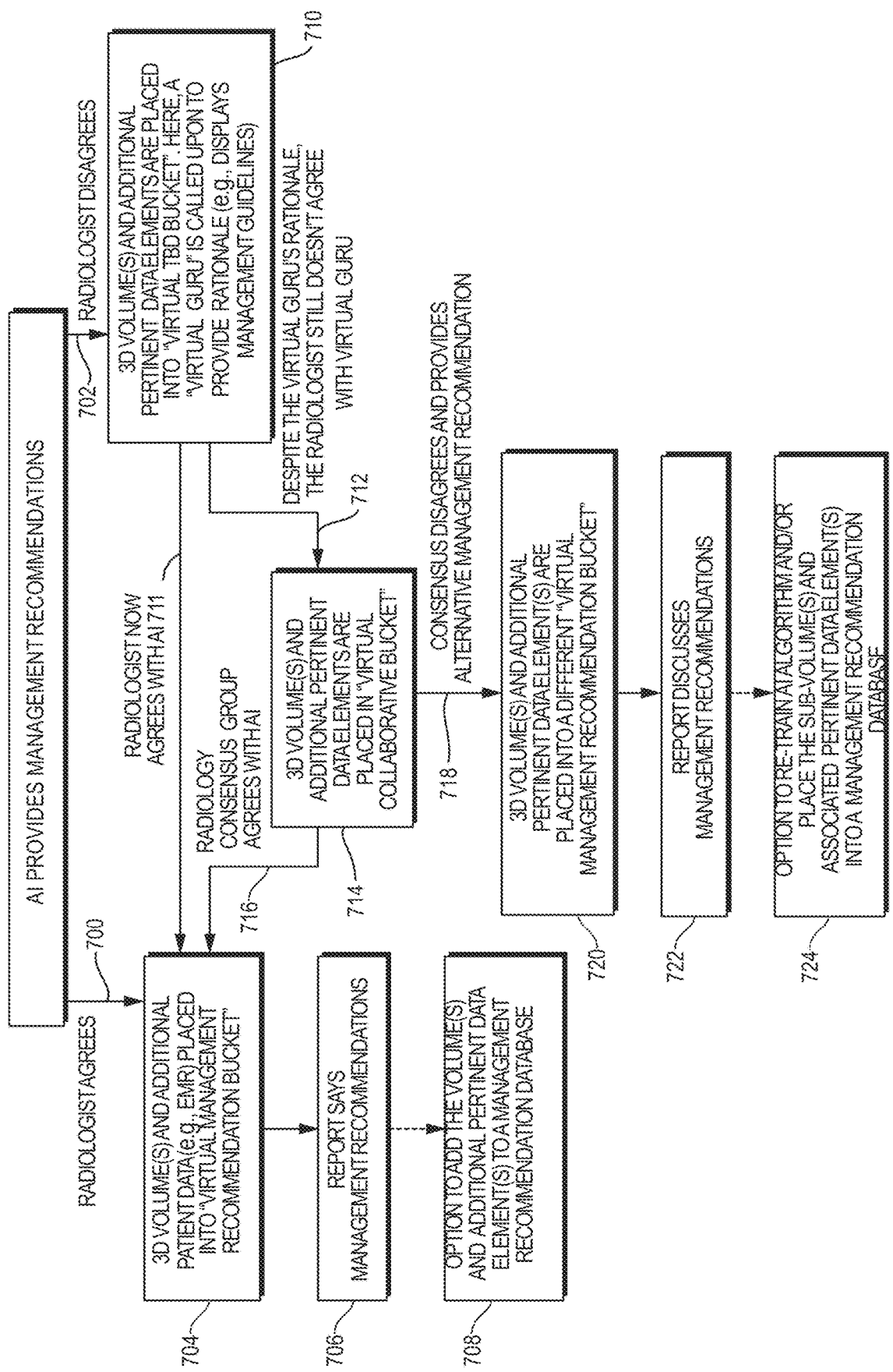
FIG. 7 illustrates a flow diagram for radiologist-assisted machine learning for the scenario wherein the AI reviews the examination and provides further management recommendations.

FIG. 7 illustrates a flow diagram for radiologist-assisted machine learning for the scenario wherein the AI reviews the examination and provides management recommendations. If the radiologist agrees with the AI 700, then the 3D volume(s) and additional pertinent data (e.g., data from the Electronic Medical Record (EMR)) are together placed into the "virtual management recommendation bucket" 704. The radiology report states the management recommendation 706. Then, an option is to add the volume and additional pertinent data element(s) to a management recommendation database 708. If the radiologist disagrees with the AI 602, then the 3D volume(s) and additional pertinent data elements are placed into "virtual TBD bucket" 710. Here, a "virtual guru" is called upon to provide rationale (e.g., displays management guidelines). If the radiologist now agrees with the AI 711, then the 3D volume(s) and additional pertinent data element(s) are added to the "virtual management recommendation bucket" 704. If, despite the virtual guru's rationale, the radiologist still doesn't agree with the virtual guru 612, then the 3D volume(s) and additional pertinent data element(s) are placed into a "virtual collaborative bucket" 714. If the radiology consensus group agrees with the AI 716, then the 3D volume(s) and additional pertinent data element(s) are added to the virtual management recommendation bucket" 704. If the radiology consensus group disagrees and believes an alternative management recommendation is warranted 718, then the 3D volume(s) and additional pertinent data element(s) are placed into a different "virtual management recommendation bucket" 720. Then, the radiology report discusses the management recommendations 722. An option at this juncture is to re-train the AI algorithm and/or place the sub-volume(s) and associated pertinent data element(s) into a management recommendation database 724.

Figure 8:
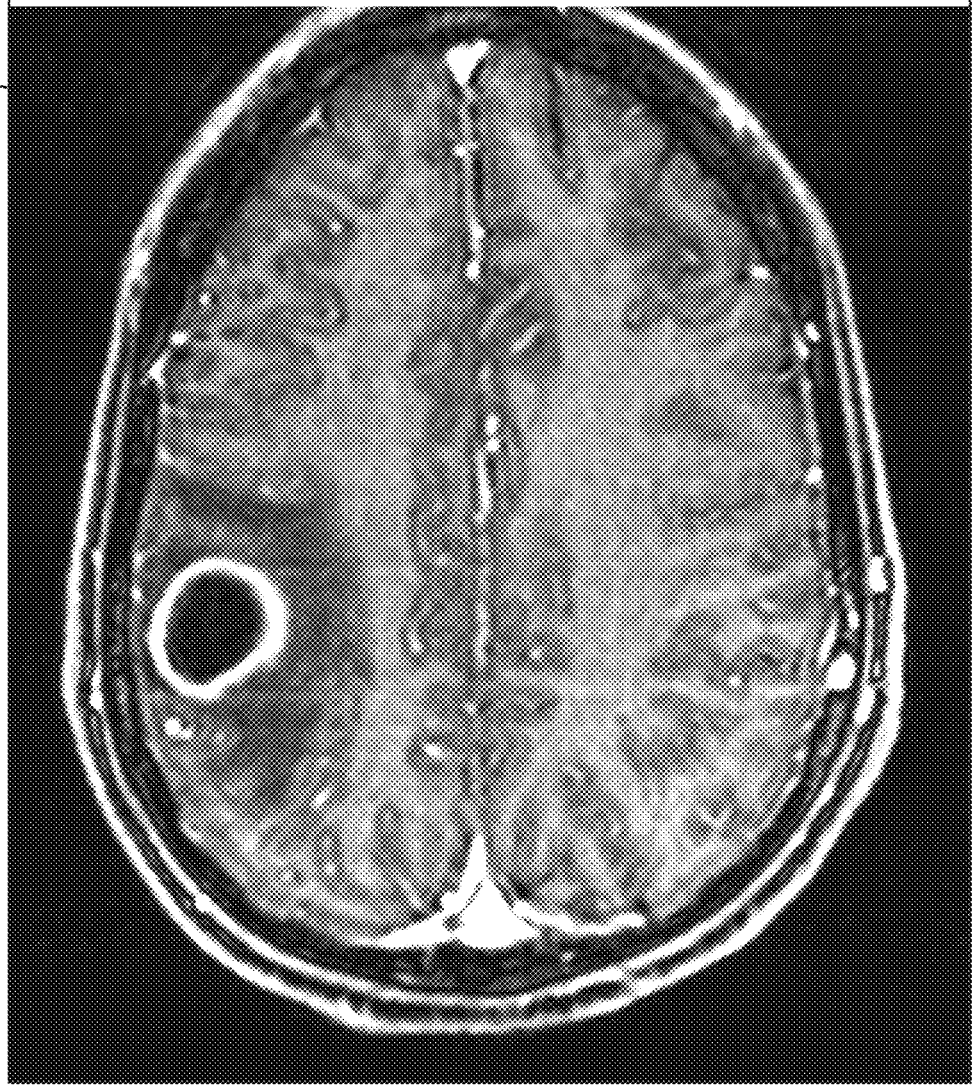
FIG. 8 illustrates the presentation of pertinent data identified via AI search through the electronic medical record that may be relevant to the area of interest that is being examined.

FIG. 8 illustrates the presentation of pertinent data identified via AI search through the electronic medical record that may be relevant to the area of interest that is being examined. The text box is shown in gray 800 and is located above the image 802. In this illustration, the AI has processed the images and has a differential diagnosis including a lung cancer metastasis to the brain. Therefore, it presents multiple potentially relevant data elements to lung cancer in the gray box. Data elements related to other differential diagnoses can also be brought in by the AI algorithm. This process serves to help mitigate some of the potential flaws in the operational system within many medical facilities. First, the physician ordering the medical images may fail to enumerate all the relevant factors impacting the patient's condition. Next, the radiologist must change tasks to obtain different information to obtain the patient's medical records. It is time-consuming to pour through the medical records to extract data that may be relevant. In the presently disclosed system the AI program obtains and processes the records, including but not limited to medical records and patient questionnaires completed upon entry to the medical facility, to obtain information relevant to the patient. Then, this data can be displayed on a conventional 2D monitor or on the headset and manipulated by the radiologist via keyboard or controller.

FIG. 9 provides a flow diagram and illustration for using the 3D cursor in conjunction with radiologist-assisted machine learning. First, as indicated in 900, 2D image slices of medical images 112 to generate a 3D volume 113 per USPTO U.S. Pat. No. 8,384,771. The 2D slices are medical images of a type which may include, but is not limited to, MRI, CT, PET, SPECT. The 2D images include pixels with a known inter-pixel spacing and known inter-slice spacing. Centered around each pixel a 3D voxel (e.g., a cube) is created with dimensions in the XY plane equal to the inter-pixel spacing and the Z direction equal to the inter-slice spacing. Next, as indicated in 902, select and encapsulate a sub-volume with a 3D cursor 130. An option at this juncture is to isolate the tissue of interest within the 3D cursor 130, which can be performed via segmentation (i.e., classifying voxels within the volume into discrete tissue types) and then performing filtering (i.e., removing voxels of non-interest and therefore improving visualization of deeper structures when taking an augmented reality, mixed reality or virtual reality 3D imaging approach) per USPTO patent application Ser. No. 15/878,463. As indicated in 904, computer aided detection (CAD)/artificial intelligence (AI) is performed on the volume subtended within the 3D cursor 130. As shown, with the exception of the liver, all tissues within the black dashed line 3D cursor 330 have been segmented and filtered (i.e., removed). A small abnormality 910 can be seen within the liver. As indicated in 906, CAD/AI identified abnormality is presented to the radiologist. For example, the conventional cross-sectional images 112 and/or via an additional 3D cursor virtual reality/augmented reality/mixed reality display 106 with reference lines. Note that further segmentation and filtering can be performed, and the isolated abnormality presented in a smaller green dashed line, cube shaped 3D cursor 130. Note that a danger level and certainty level are also provided as detailed in FIG. 12. Finally, as indicated in 908, the radiologist(s) analyze the imaging findings and performs feedback for machine learning.

Figure 10:
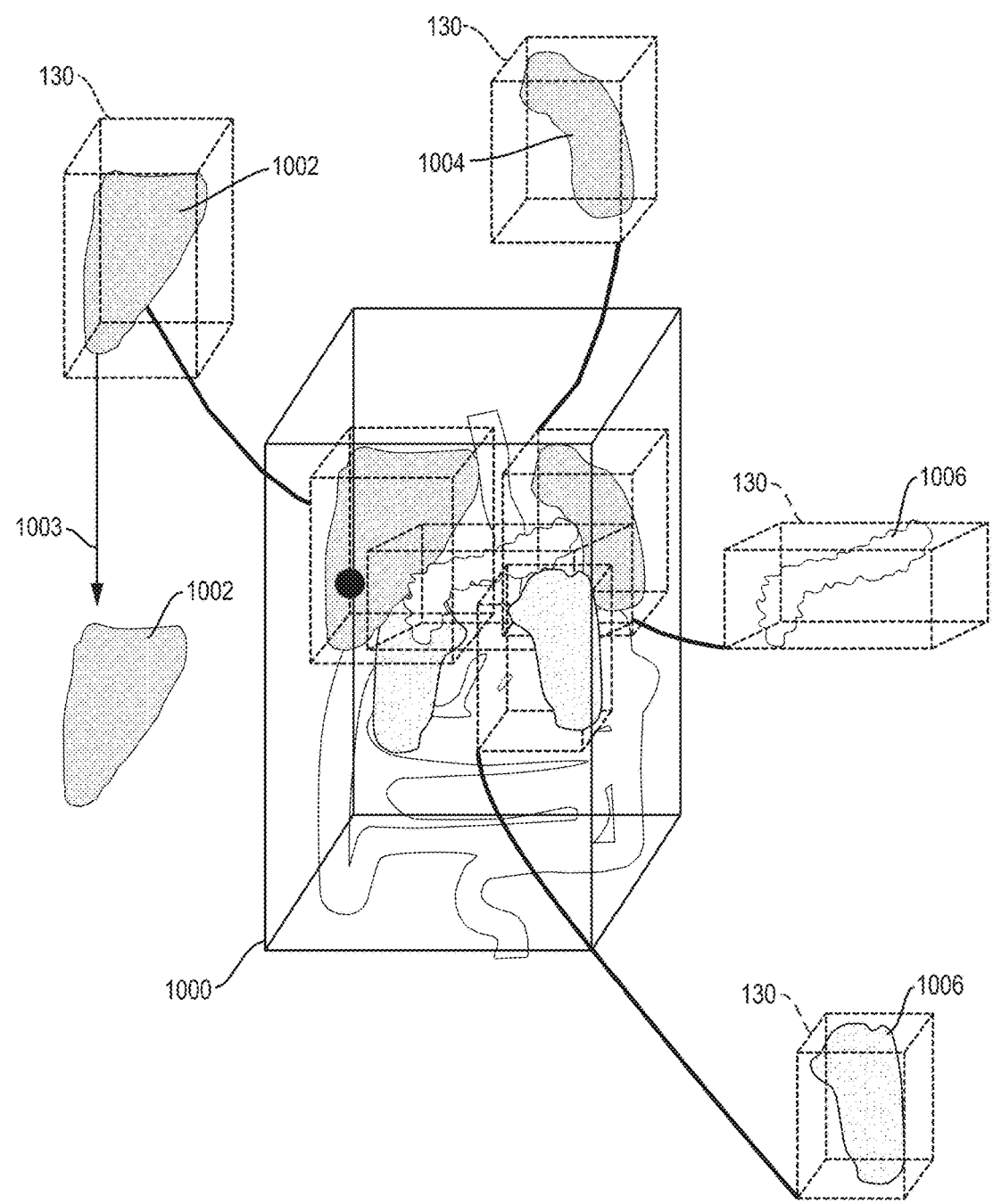
FIG. 10 illustrates the relationship between the composite volume, a sub-volume and volume subtending 3D cursor.

FIG. 10 illustrates the relationship between the composite volume, a sub-volume and volume subtending 3D cursor. In the illustration, multiple shapes of varying shades of gray represent organs of the abdomen and pelvis in the total imaging volume (also referred to as the composite imaging volume) as denoted by 1000. Multiple 3D cursors 130 are shown with each cursor displaying a sub-volume (i.e., a portion of the composite imaging volume). For example, one 3D cursor 130 contains the sub-volume of the liver 1002 with all other tissues within the 3D cursor 130 segmented and filtered (i.e., removed). While the preferred method to visualize and analyze sub-volumes is to keep each sub-volume contained within a 3D cursor, it is also possible to visualize and analyze a sub-volume without being contained in a 3D cursor 130, as shown in 1003. Another example includes a 3D cursor 130 containing the sub-volume of the spleen 1004 with all other tissues within the 3D cursor 130 segmented and filtered (i.e., removed). Another example, includes a 3D cursor 130 containing the sub-volume of the pancreas 1006 with all other tissues within the 3D cursor 130 segmented and filtered (i.e., removed). Finally, another example includes a 3D cursor 130 containing the sub-volume of the left kidney 1006 with all other tissues within the 3D cursor 130 segmented and filtered (i.e., removed). The sub-volumes can each be inspected carefully in the traditional slice-by-slice cross-sectional approach or via advanced 3D viewing such as with an augmented reality headset 106. The diagnostic system provides the radiologist with the capability to review one sub-region by sub-region (i.e., 3D cursors of a size specified by the radiologist for an efficient review) throughout the volume being reviewed in accordance with the check list. Further, the radiologist may decide to move the volume-subtending 3D cursor through the total imaging volume without a discrete organ-by-organ checklist. In this situation, a composite view of cursor path through the 3D volume and re-positioning cursor to initial viewing position can be performed. When the AI/CAD algorithm has identified, the radiologist conducting the review will place special attention to these regions. These regions will be sent to the virtual report bucket (or other bucket) in accordance with the features described throughout this patent. After the review is completed, the radiologist can verify the completeness of the review by invoking display of all of the 3D cursor positions simultaneously. This feature enables the radiologist to see if any portions of the imaging volume that might have been missed during the review and go back, as necessary, to ensure completeness of the review. This process will help ensure a low error rate for the review.

Figure 11:
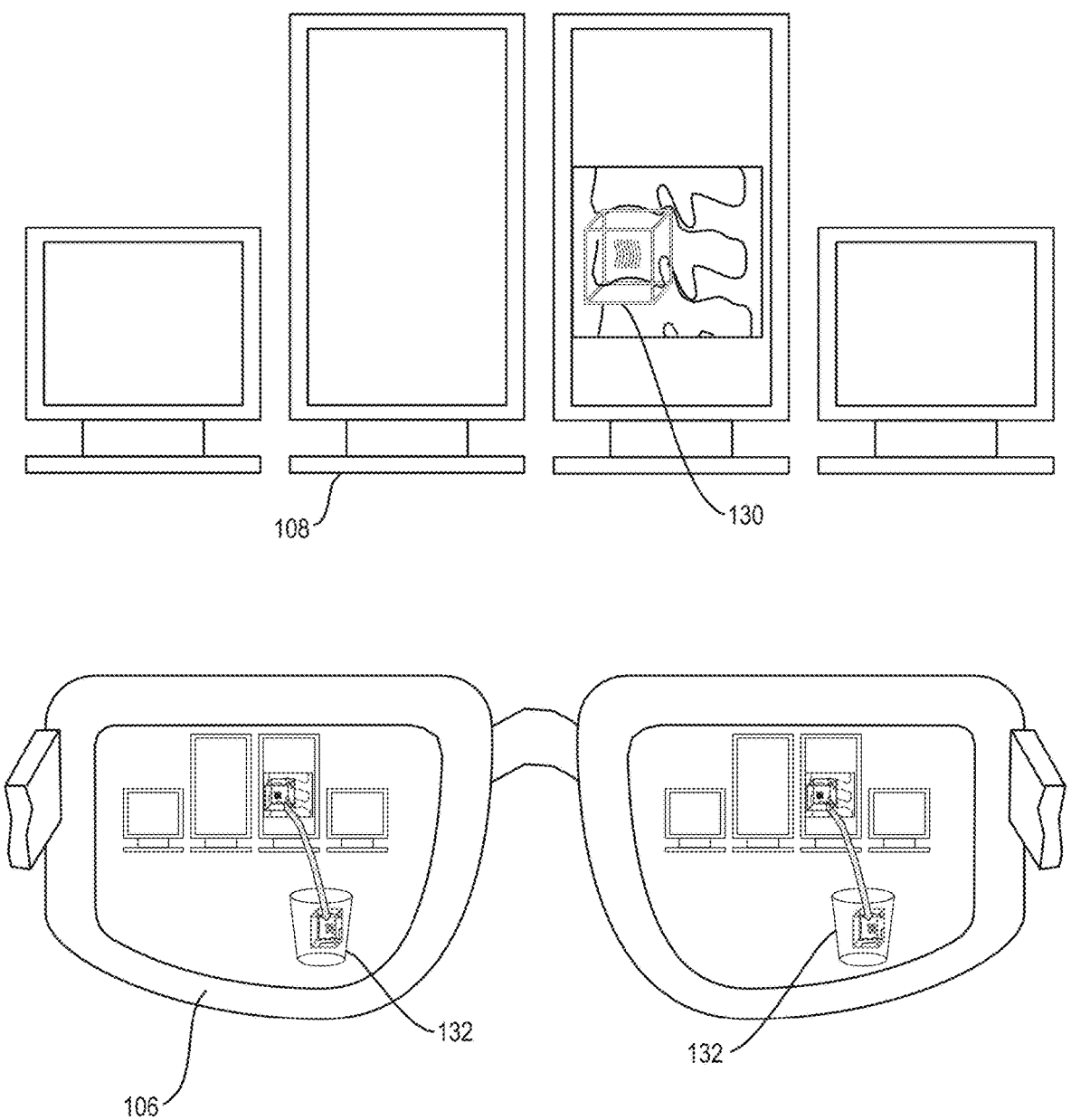
FIG. 11 illustrates the radiologist's workstation without (top) and looking through (bottom) an augmented reality headset where the radiologist can see the virtual bucket only when looking through the augmented reality (AR) display.

FIG. 11 illustrates the radiologist's workstation without (top) and looking through (bottom) an augmented reality headset where the radiologist can see the virtual bucket only when looking through the AR display. The radiologist would have the ability to virtually pull a selected sub-volume out of the total volume and then place it into a virtual bucket. The preferred approach would be for the radiologist to utilize augmented reality glasses 106 where the radiologist could see virtual buckets on or near his workstation. However, if the radiologist workstation did not have augmented reality glasses, an icon to represent the "virtual bucket" can be used on conventional 2D monitors.

Figure 12:
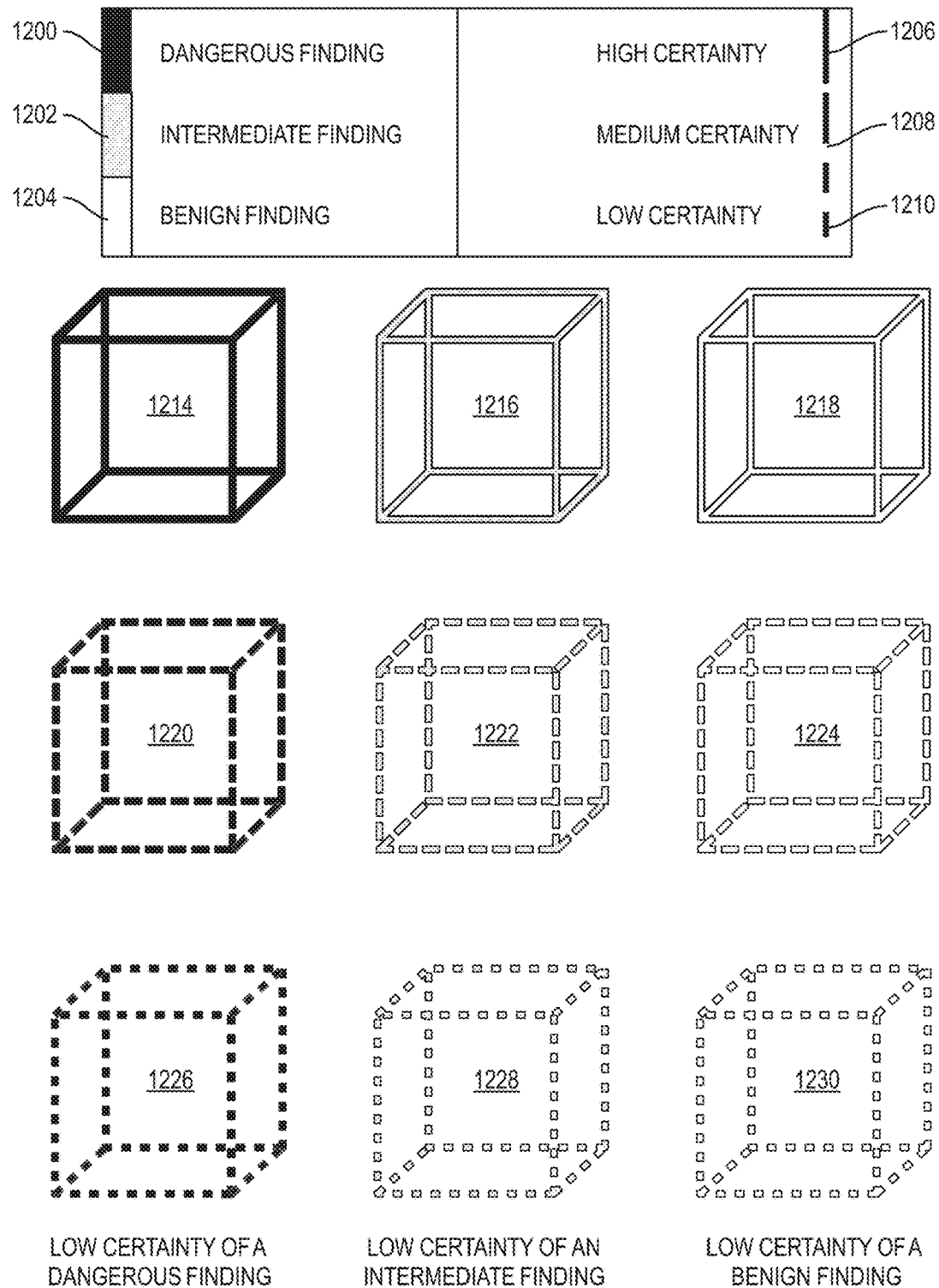
FIG. 12 illustrates an example of how the 3D cursor appearance can change to denote certainty level and severity level of an imaging finding within a sub-volume.

FIG. 12 illustrates an example of how the 3D cursor appearance can change to denote certainty level and severity level of an imaging finding within a sub-volume. The AI and/or CAD performs an initial analysis of the image set. Two key critical pieces information that the radiologist needs to know are the danger of the finding(s) and the certainty level of the finding(s). These two critical pieces can be communicated by changing the appearance of the cursor. The line defining the margins of the 3D cursor can be color-coded to correspond to the danger level of the findings, such as red to denote a dangerous finding (defined as reasonable chance of causing death) 1200, yellow to denote an intermediate finding (defined as likely to cause symptoms, but unlikely to cause death) 1202, and green to denote a benign finding (defined as unlikely to cause symptoms or death) 1204. In addition, the line defining the margins of the 3D cursor can appear solid to correspond to a high level of certainty 1206, dashed to correspond to a medium level of certainty 1208 or dotted to correspond to a low level of certainty 1210. Thus, there are multiple combinations. A red, solid 3D cursor 1214 would indicate high certainty of a dangerous finding. A yellow, solid 3D cursor 1216 would indicate high certainty of an intermediate finding. A green, solid 3D cursor 1218 would indicate a high certainty of a benign finding. A red, dashed 3D cursor 1220 would indicate medium certainty of a dangerous finding. A yellow, dashed 3D cursor 1222 would indicate a medium certainty of an intermediate finding. A green, dashed 3D cursor 1224 would indicate a medium certainty of a benign finding. A red, dotted 3D cursor 1226 would indicate low certainty of a dangerous finding. A yellow, dotted 3D cursor 1228 would indicate low certainty of an intermediate finding. A green, dotted 3D cursor 1230 would indicate low certainty of a benign finding. A preferred option would be for no 3D cursor to be displayed if a checklist item (e.g., organ) has normal findings. When a radiologist opens up a new case, he/she may select "show all red cursors" to see if there are any life-threatening findings and if applicable, notify the ordering physician immediately. During the review process, the radiologist(s) can, on his/her discretion, override the AI/CAD system and change the appearance (color or style of line) such that ordering physicians can see both the AI set of 3D cursors and the radiologist-adjusted set of 3D cursors.

Figure 13:
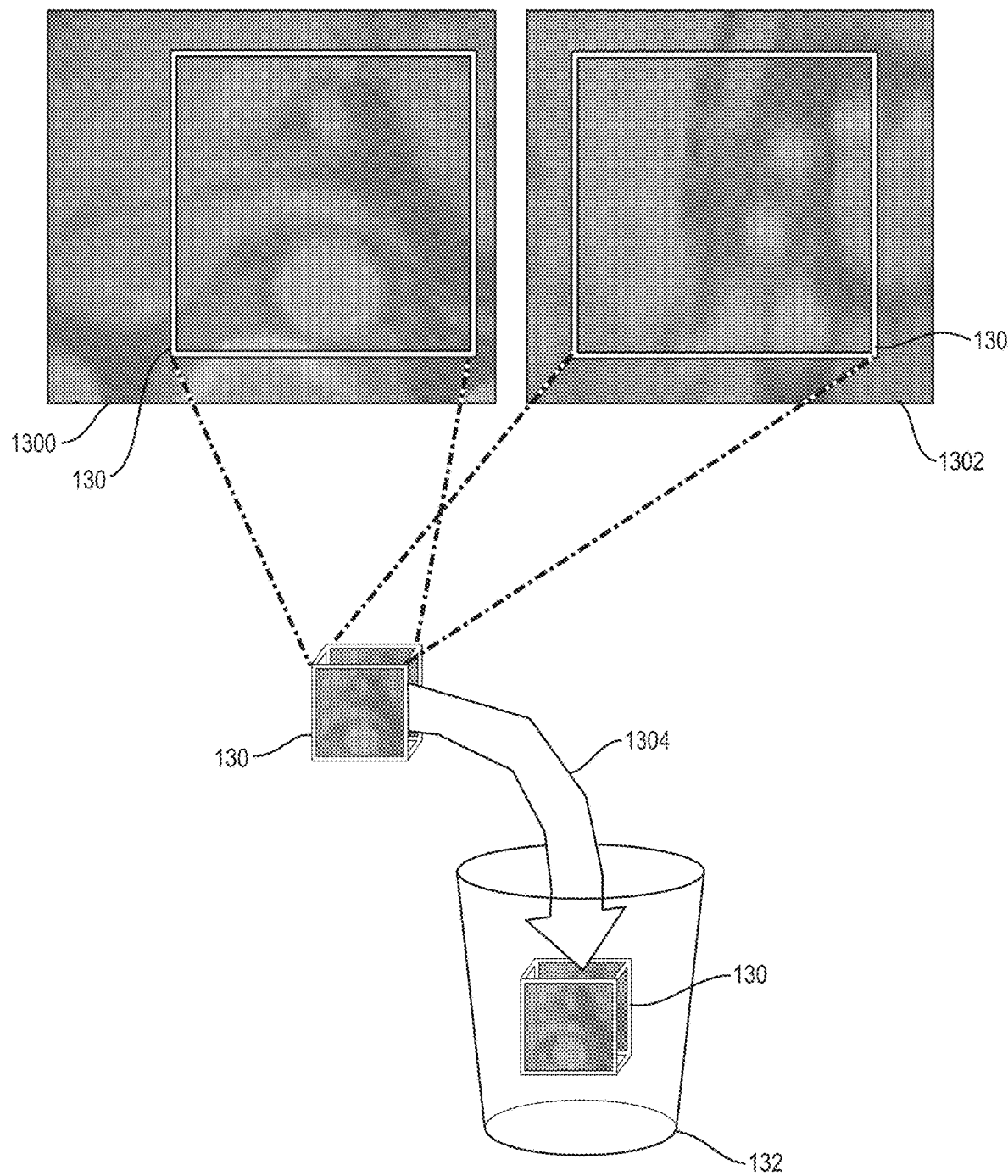
FIG. 13 illustrates placing a normal sub-volume into a "normal anatomy bucket" aspect of radiologist-assisted training.

FIG. 13 illustrates placing a normal sub-volume into a "normal anatomy bucket" aspect of radiologist-assisted training. Axial 1300 and image 1302 contrast enhanced computed tomography (CT) images through the abdomen. Both the axial and coronal images show portions of the superior mesenteric artery (SMA) including the origin and proximal portions. As illustrated, the 3D cursor 130 is used to encapsulate relevant tissue to isolated the sub-volume from the total imaging volume within the CT of the abdomen examination. After encapsulating the origin and proximal portions of the SMA, the radiologist can generate a duplicate copy of the sub-volume within the 3D cursor containing a normal SMA and move 1304 the copied sub-volume within the 3D cursor 130 into a virtual bucket 132, which in this case would be the normal SMA origin contrast-enhanced CT virtual bucket 132. This process of dividing an examination's total imaging volume into sub-volumes and placing sub-volumes into specific bucket can be used for creating radiologist-approved training datasets, which can, in turn, be used to train machine learning algorithms.

Figure 14:
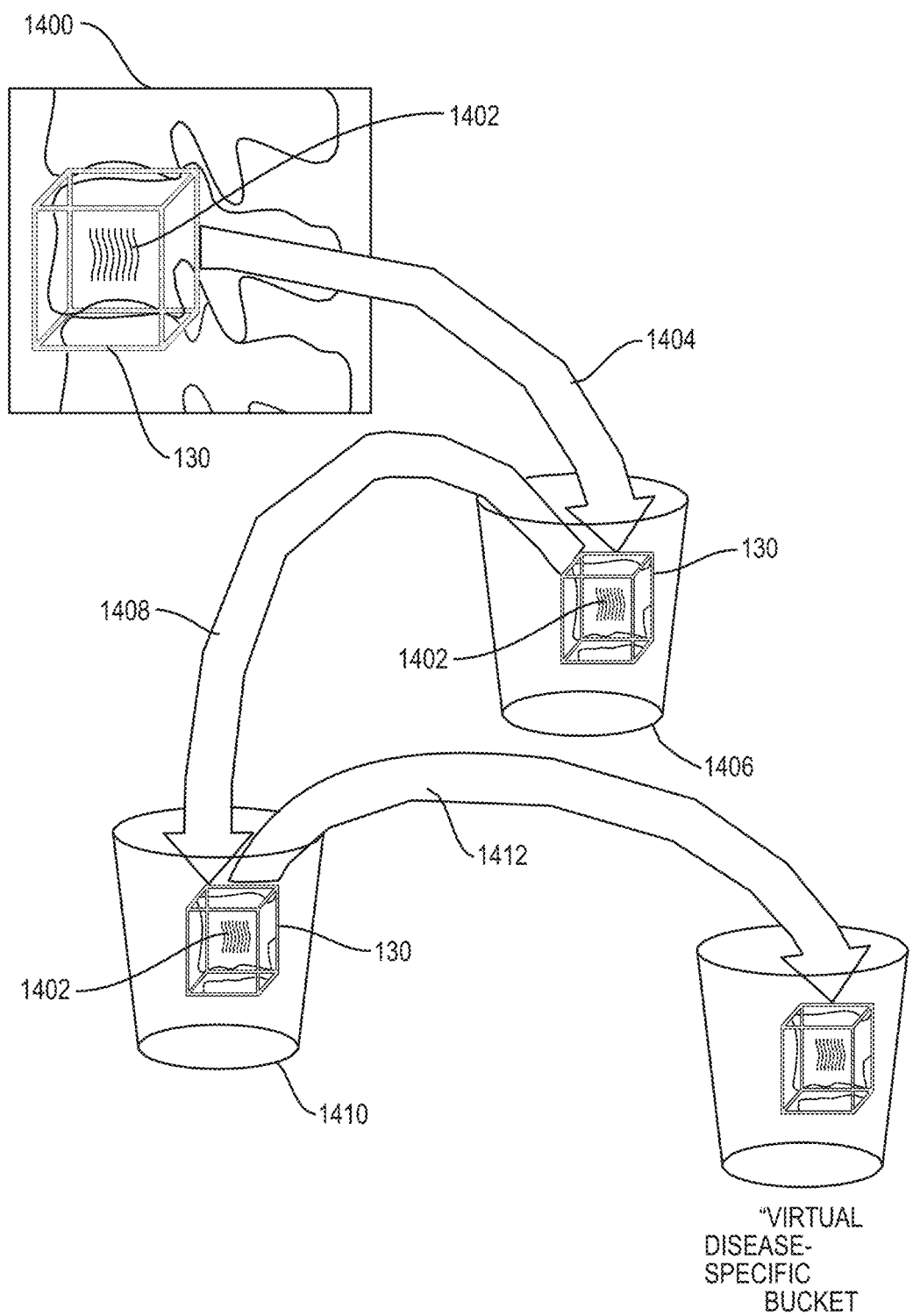
FIG. 14 illustrates the use of the virtual bucket system whereby a volume subtended by a 3D cursor can be moved from one bucket to the next during the analysis phase.

FIG. 14 illustrates the use of the virtual bucket system whereby a volume subtended by a 3D cursor can be moved from one bucket to the next during the analysis phase. During a radiologist review, there may occur multiple clusters of tissue of interest/concern and multiple clusters of tissue that is not of concern. In this scenario, the AI determines that the total imaging volume 1400 is normal, but the radiologist thinks there is an abnormality 1402, but is unsure of what it could be. Therefore, the radiologist places 1404 the 3D cursor 130 containing a sub-volume and the structure of interest 1402 into the "virtual TBD bucket" 1406. The radiologist calls upon the "virtual guru" to find specifically analyze the tissue within the sub-volume encased by the 3D cursor 130. In this scenario, the "virtual guru" concludes that the sub-volume encased by the 3D cursor 130 is normal. The radiologist then places 1408 the 3D cursor 130 and its contents to the "virtual collaborative bucket" 1410. Here a group of radiologists get together, and the consensus is that the structure of interest 1402 within the 3D cursor is a benign vertebral hemangioma. They, the radiologist places 1412 the sub-volume within the 3D cursor into the "benign vertebral hemangioma" virtual bucket 1414. The radiologist may also elect to assign terminology (e.g., "corduroy sign" and "vertebral hemangioma") weighting factors (e.g., "95% certainty") (see FIG. 16 for additional details). Another key benefit of this approach would be the utilization of a "bucket" system for radiologist peer review processes. Peers could review "normal anatomy buckets" for accuracy. Alternatively, they could review "virtual disease specific buckets" for accuracy. Bucket accuracy would be a key factor in determining the skill level of a radiologist.

FIG. 15 illustrates an example radiology report incorporating the 3D cursor and radiologist-assisted machine learning reporting technique. The left hand portion contains each of the checklist items. The column to the right shows the results of each finding on the checklist. For each abnormal finding, an image of the segmented and filtered checklist item is displayed with the 3D cursor with appearance to denote danger and certainty levels is shown at the abnormality. The right-hand portion contains a description of the abnormal findings. If the reviewing the report on a computer, the headset glasses provide a hyper link to volume containing the organ and abnormality encapsulated in the 3D cursor. It is important to note that there must be consistency between the findings within the abdomen. For example, a round sub-centimeter lymph node may be passed by the AI algorithm during the first check. Then, the AI algorithm may, at a later item on the checklist, diagnose a cancerous tumor. Then, the AI algorithm should return through the checklist additional time(s) to re-evaluate all structures in light of the cancerous tumors. For example, a 9 mm round lymph node may on first pass be characterized as benign by the AI algorithm. Then, a cancer is diagnosed. Then, on second pass, the same 9 mm round lymph node may on second pass be characterized as suspicious for metastatic disease.

Figure 16:
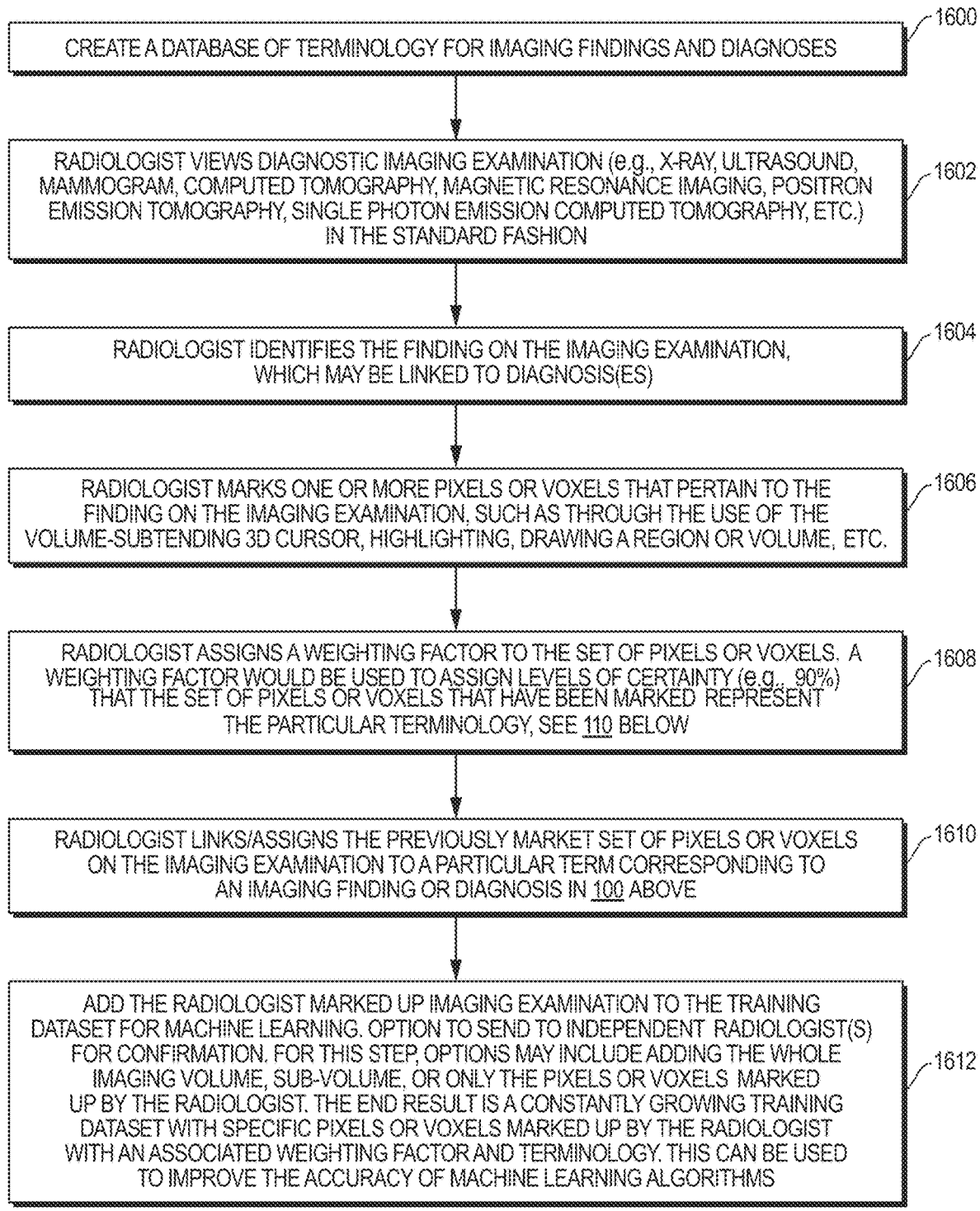
FIG. 16 illustrates a process for creating a radiologist approved machine learning training dataset by incorporating standardized terminology, radiologist image markup and radiologist-assigned weighting factors for radiologist-assisted machine learning.

FIG. 16 illustrates a process for creating a radiologist approved machine learning training dataset by incorporating standardized terminology, radiologist image markup and radiologist-assigned weighting factors for radiologist-assisted machine learning. Machine learning may be based on radiologist review and AI/CAD used to partially automate diagnostic review. In step 1600 a database of terminology is created for image findings and diagnosis. In step 1602 the radiologist views a diagnostic imaging examination in a standard manner using a radiologic imaging and diagnostic system. In step 1604 the radiologist identifies a finding which may be linked to a diagnosis(es) on an imaging examination using the radiologic imaging and diagnostic system. In step 1606 the radiologist marks one or more pixels or voxels of an image that pertain to the finding. This can be through the use of the volume-subtending 3D cursor, highlighting, or drawing a region around the area or volume. In step 1608 the radiologist assigns a weighting factor to the marked set of pixels or voxels. In step 1610 the radiologist links the marked set of pixels or voxels to a term corresponding to a finding or diagnosis as in step 1600 above. In step 1612 the report, pixels and/or voxels marked by the radiologist and associated with a weighting factor, and the terminology are added to a training dataset for machine learning by the imaging and diagnostic system. Options may include adding the whole imaging volume, sub-volume, or only the pixels or voxels marked by the radiologist. The end result is a training dataset with specific pixels or voxels marked up by the radiologist with an associated weighting factor and terminology. This can be used to improve the accuracy of machine learning algorithms.

Figure 17:
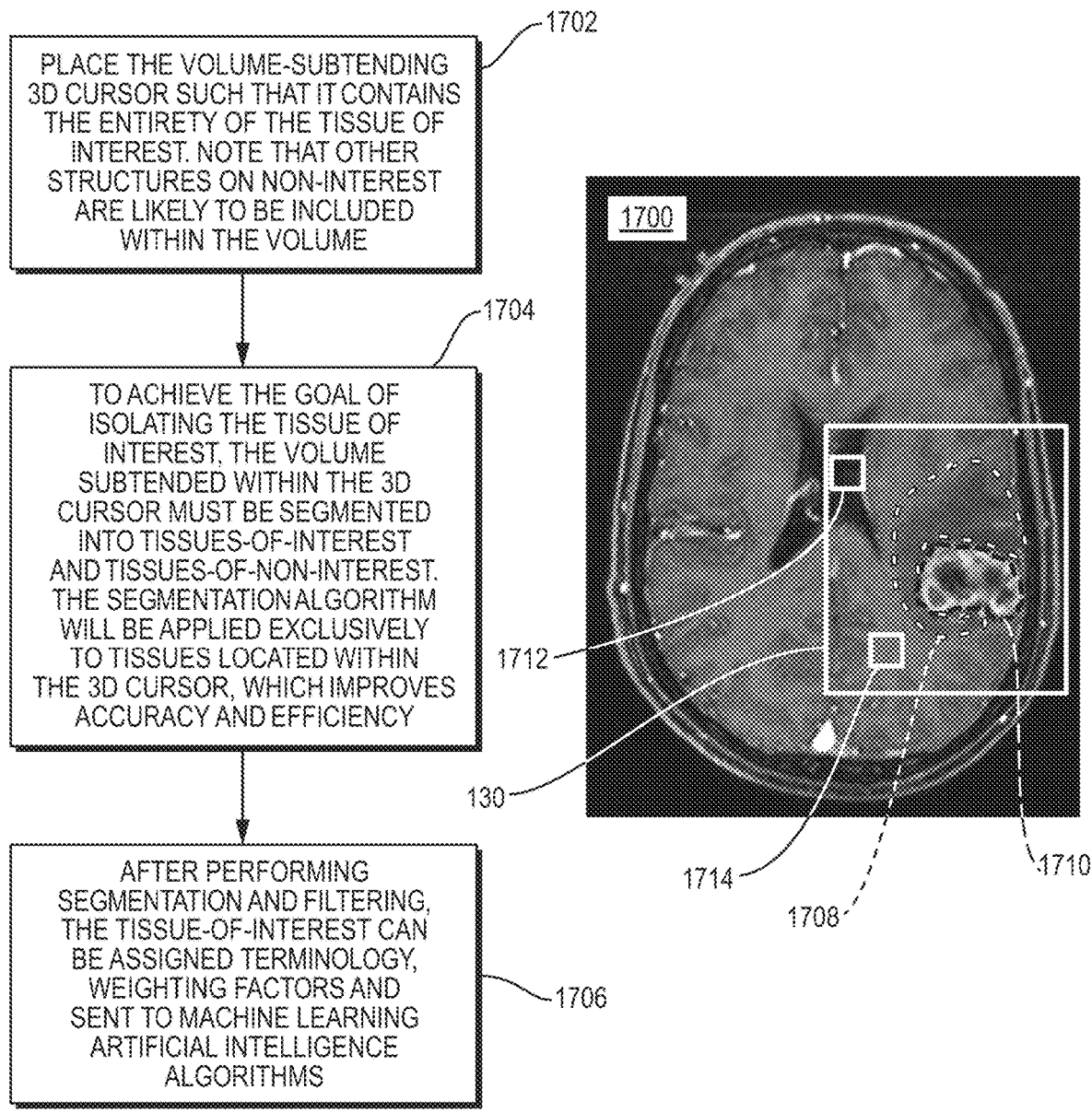
FIG. 17 is a flow diagram and illustration of use of multiple 3D cursor to assist segmentation used in conjunction with radiologist-assisted machine learning via labeling with terminology and weighting factors for radiologist-assisted machine learning.

FIG. 17 is a flow diagram and illustration of use of multiple 3D cursor to assist segmentation used in conjunction with radiologist-assisted machine learning via labeling with terminology and weighting factors for radiologist-assisted machine learning. This can help the AI system can begin to understand that one pathology (e.g., brain tumor) can have multiple components (e.g., non-enhancing component and enhancing component). An efficient segmentation algorithm will help the adoption of RAML into clinical practice. The illustrated example is a 2D MRI slice of a brain 1700 which has a tumor. Segmentation algorithms can be applied to define anatomic structures and/or different components of the tumorous material. Using the controller, the radiologist configures for display the tissue of concern and/or tissue associated with a checklist item. The first step 1700 is to place the 3D cursor 130 over a large volume/area including the entire object of interest, e.g. tumor, and additional tissues of non-interest. To accomplish this, a radiologist can move, size and shape a volume-subtending 3D cursor 130 over a region sufficiently large to encompass the entire brain tumor. In doing this, components of normal brain tissue, cerebrospinal fluid, skull, scalp and air outside of the head will typically be included inside the volume-subtending 3D cursor 130. The second step 1704, the utilization of a 3D cursor 130 can add efficiency and accuracy to this process, by applying a segmentation algorithm only to structures that are within the 3D cursor 130. Then, the margins of the different components of the tumor can be defined (either by the radiologist or by a computer-segmentation algorithm). For example, the segmentation algorithm can divide the tumor into a non-enhancing component 1708 and an enhancing component 1710. To further assist with isolating the tumor, other structures can be labeled and subsequently filtered. For example, a small 3D cursor marks the cerebrospinal fluid 1712. Also, a small 3D cursor marks the normal white matter 1714. The segmented components can be used to train future AI algorithms via the virtual bucket system in the RAML process. After performing segmentation, the tissue of interest can be assigned terminology, weighting factors and used to improve artificial intelligence algorithms 1706. As an example, 3D cursor 1712 containing pixel(s) or voxel(s) of non-interest can be labeled with terminology (e.g., "normal CSF appearance on T1-FSPGR post-contrast sequence", etc.) and weighting factor (e.g., 100% based on neuroradiologist's experience). Also, segmented pixels (or voxels) of interest (i.e., enhancing component of the brain tumor 1708 and non-enhancing component of the brain tumor 1710) can be labeled with terminology (e.g., "enhancing component of glioblastoma multiforme" and "non-enhancing component of glioblastoma multiforme") and weighting factor (e.g., 100% given biopsy and pathology proven).

Figure 18:
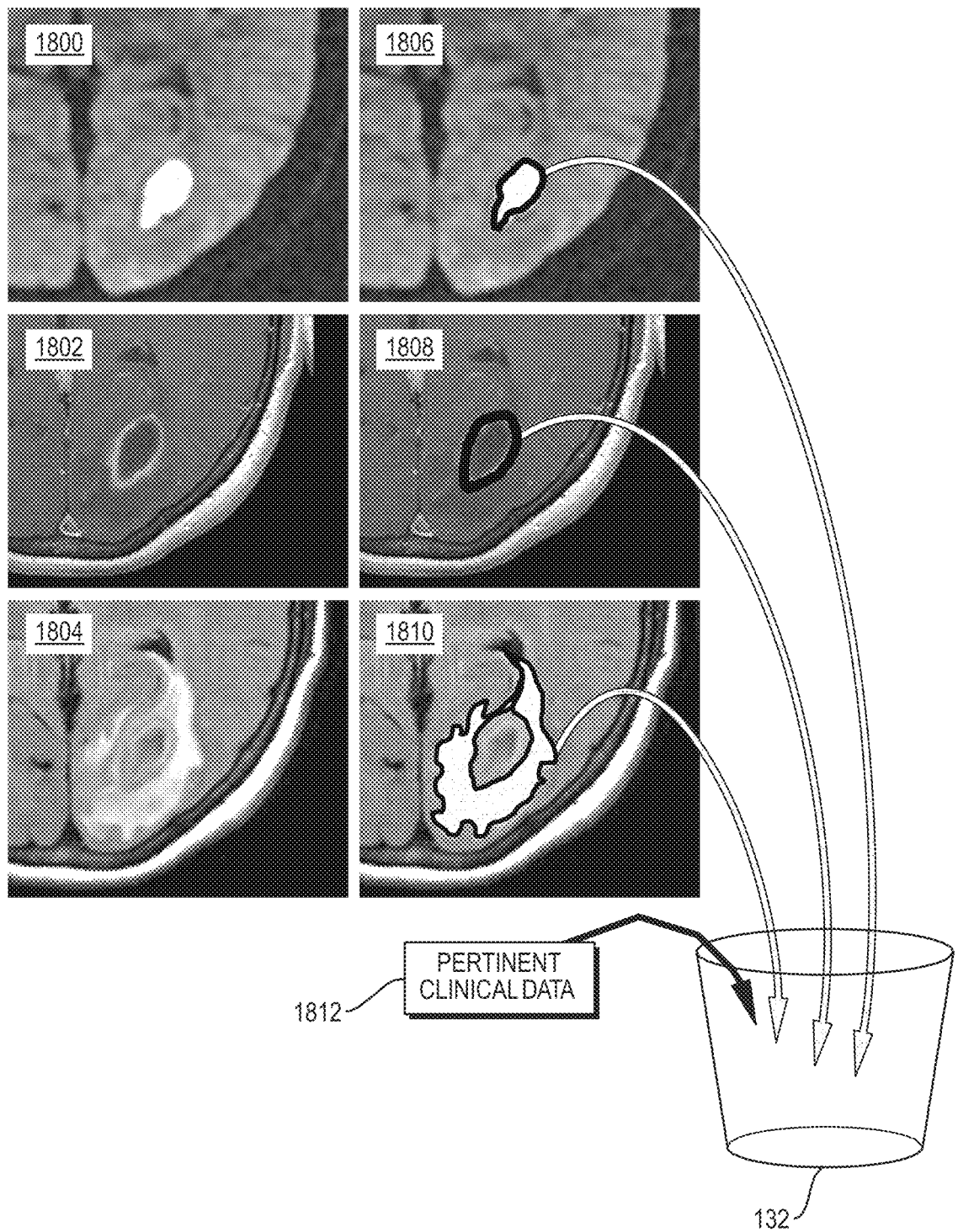
FIG. 18 illustrates image markup and terminology assignment in conjunction with radiologist-assisted machine learning.

FIG. 18 illustrates image markup and terminology assignment in conjunction with radiologist-assisted machine learning. In this figure, three different MRI sequences of the brain were obtained. The top left is a diffusion weighted image 1800. The middle left is a post-contrast T1-weighted image 1802. The bottom left is a T2-weighted FLAIR image 1804. The key pixels on the diffusion image have been marked up by a radiologist 1806, assigned imaging finding terminology (i.e., "central restricted diffusion") with an associated certainty level (i.e., there is a 95% certainty that the marked pixels represent true "central restricted diffusion"), assigned a diagnosis terminology (i.e., "brain abscess") with an associated certainty level based on the imaging terminology finding (i.e., in the literature, it is reported that the sensitivity and specificity of the imaging finding of "central restricted diffusion" for the diagnosis of "brain abscess" is 96% and 96%, respectively). Similarly, the key pixels on the post-contrast T1-weighted image are marked up by a radiologist 1808, assigned imaging finding terminology (i.e., "peripheral enhancement) with an associated certainty level (i.e., there is a 99% certainty that the marked pixels on the post-contrast T1-weighted MRI represent true "peripheral enhancement"), assigned a diagnosis terminology (i.e., "brain abscess") with an associated certainty level based on imaging terminology findings (i.e., in the literature, a variety of conditions can cause peripheral enhancement including brain metastases, brain abscesses, gliomas, infarction, contusion, demyelinating disease and post-radiation changes; therefore, specificity is low. Experienced radiologists consensus groups can aid in filling in holes where there is no data in the literature on the precise sensitivities and specificities.). Finally, the key pixels on the T2-weighted FLAIR image are marked up by a radiologist 1810, assigned imaging finding terminology (e.g., "surrounding vasogenic edema") with an associated certainty level (i.e., the radiologist is 90% certain that the marked pixels on the T2-weighted FLAIR image represent true "surrounding vasogenic edema"), assigned a diagnostic terminology (i.e., "brain abscess") with an associated certainty level based on imaging terminology findings (i.e., in the literature, a wide variety of conditions can cause vasogenic edema including brain abscesses, contusions, and many others. Therefore, this imaging finding is non-specific. However, since a brain abscess incites an inflammatory response in the brain, it is extremely common to have vasogenic edema and the sensitivity of vasogenic edema for the diagnosis of brain abscess is high.). Finally, pertinent clinical data (e.g. white blood cell count, vital signs, etc.) 1812 will be placed into a virtual bucket 132. After confirmation of the suspected diagnosis of a brain abscess via neurosurgery, the imaging examination, 3D cursor, markup and pertinent clinical data can be added to a database of disease specific pathology, which can be used to refine machine learning and artificial intelligence algorithms.

Figure 19:
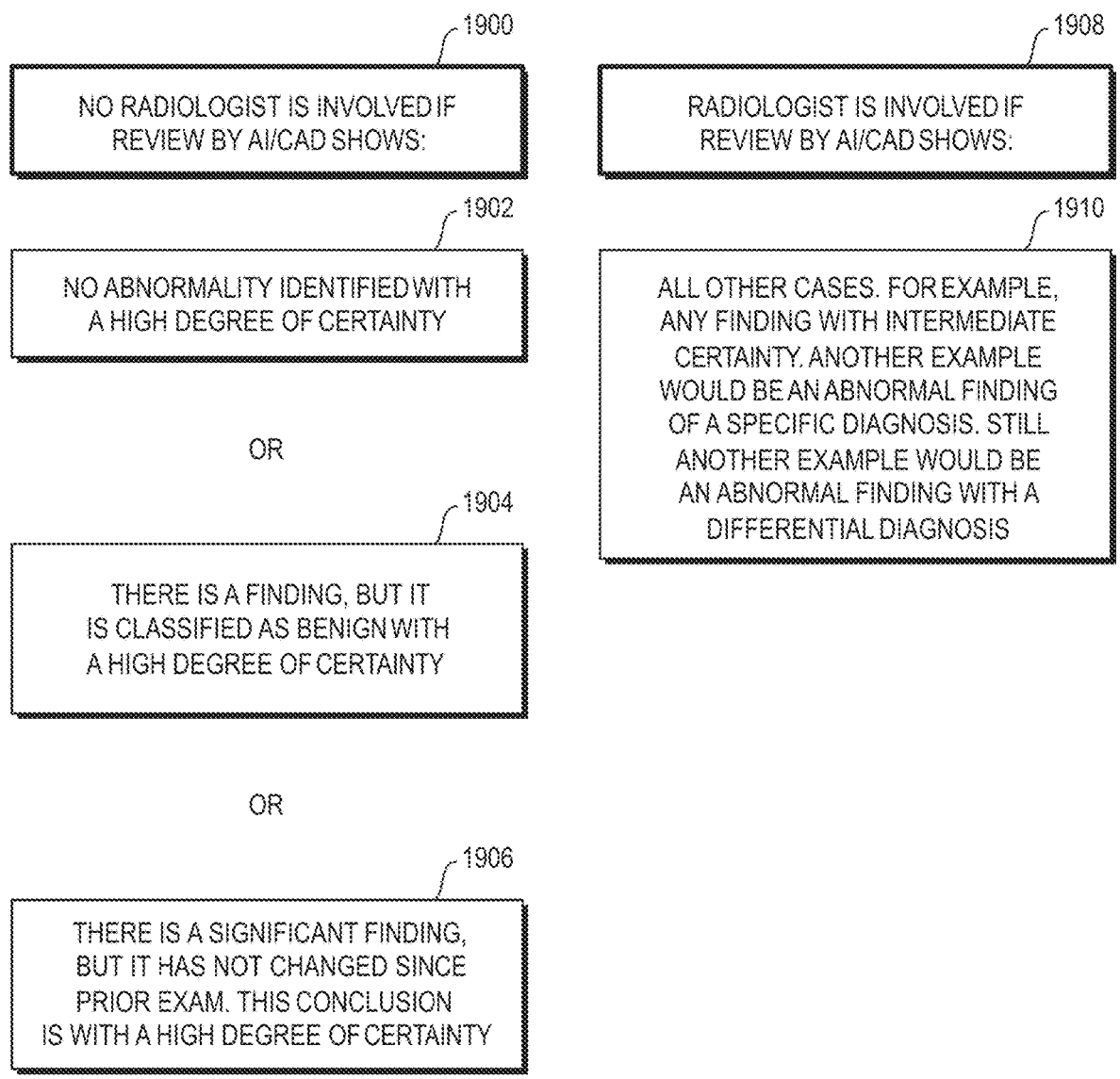
FIG. 19 illustrates a sample set of criteria wherein AI determines whether the imaging examination requires a radiologist's review.

FIG. 19 illustrates a suggested set of criteria wherein AI determines whether the imaging examination requires a radiologist's review. Note that it is conceivable that in the very near term, AI may be extremely accurate in its declaration of a normal finding. In these such situations, a revised process (updated from FIG. 3) may consist of the AI and/or CAD algorithms not requiring a review by a radiologist. However, in the current state (wherein AI is not approaching 100% detection rates), all cases would be passed to a radiologist. The system can be designed such that it does not prompt radiologist review 1900 when AI and/or CAD review concludes that no abnormality is identified 1902, or there is a benign finding classified with a high degree of certainty 1904, or there is a significant finding that has not changed since the prior diagnostic examination 1906. Each factor of the first case can be made contingent on high degree of certainty, information in the patient's reason for visit, and/or information in medical records that would cause suspicion. If the specified conditions hold then the system does not require a review by a radiologist. Radiologist review is prompted 1908 in all other cases 1910. For example, any finding with intermediate certainty would be reviewed by a radiologist. Another example would be an abnormal finding of a specific diagnosis would be reviewed by a radiologist. Still another example would be an abnormal finding with a differential diagnosis would be reviewed by a radiologist. The AI and/or CAD performs an initial diagnosis and uses decision criteria to determine which cases will undergo a radiologist review. Two factors that may be applied are: the danger level and the certainty level of the AI and/or CAD findings. All dangerous cases are provided to a radiologist for further review. Any benign case that is of high certainty is not sent for review by a radiologist. Other combinations would be a policy matter for the medical facility. However, until AI and/or CAD have proven exceptionally reliable for intermediate findings, it would be prudent to pass these cases to a radiologist. Reviewing AI and/or CAD results to date indicates different levels of accuracy for different body parts so, as the checklist is applied, differing levels of certainty will accompany different body parts.

Figure 20:
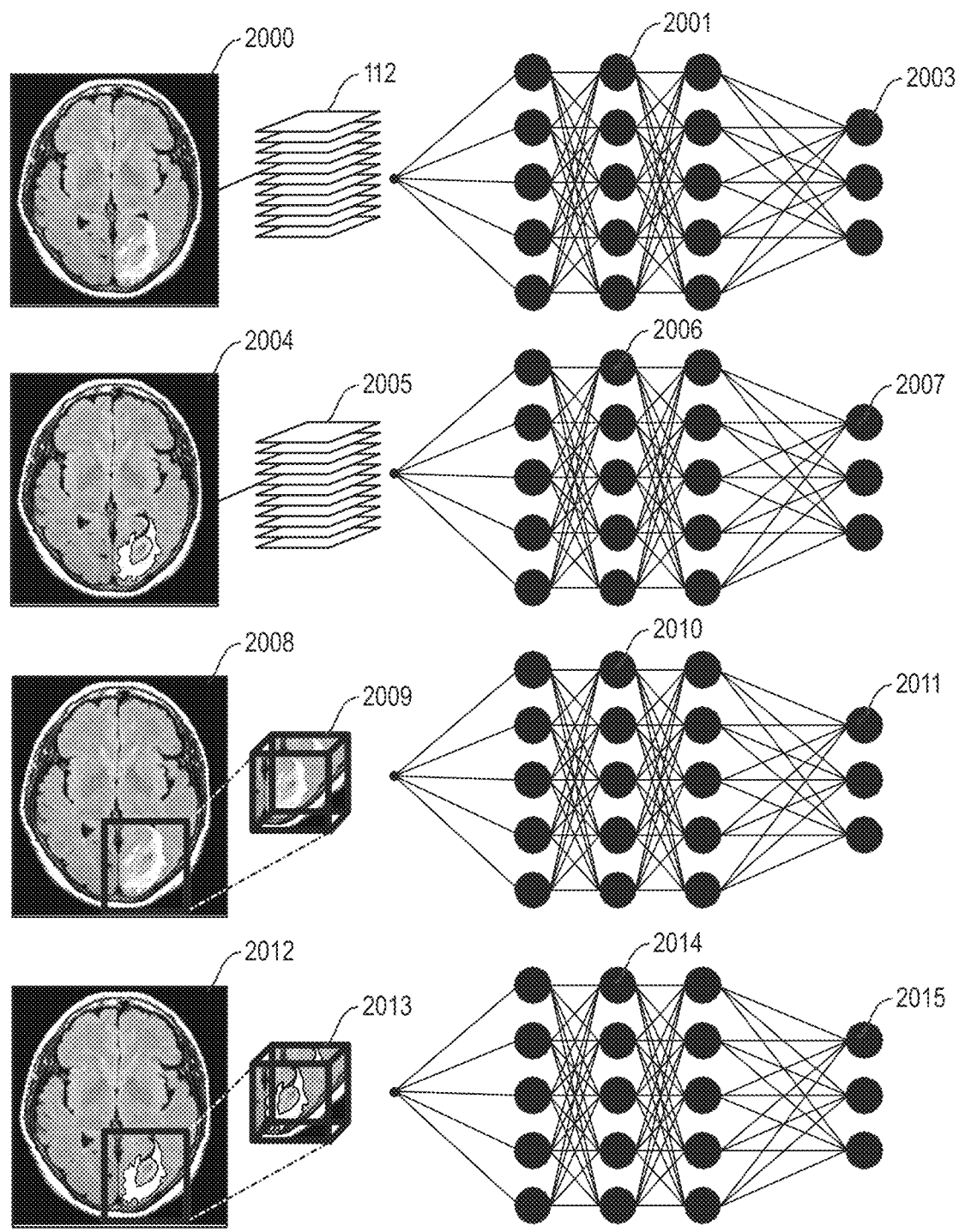
FIG. 20 illustrates the utilization of radiologist image markup and 3D cursors in deep learning algorithms.

FIG. 20 illustrates the utilization of radiologist image markup and 3D cursors in deep learning algorithms. In the first row, a single axial MRI image of the brain 2000 or stack of axial MRI images of the brain 112 can be inputted into a deep learning algorithm consisting of hidden layers 2001 to generate an output 2003 with the top three (or more) differential diagnoses shows with associated rank order or probability. In the second row, a single axial MRI image of the brain with some of the pixels marked up by the radiologist with associated terminology and weighting factors 2008 or stack of marked axial MRI images of the brain 2009 can be inputted into a deep learning algorithm consisting of hidden layers 2010 to generate an output 2011 with the top three (or more) differential diagnoses shows with associated rank order or probability. In the third row, a single axial MRI image of the brain 2008 is illustrated with the 3D cursor marking an imaging finding. A 3D cursor, which encapsulates a sub-volume 2009, can be inputted into a deep learning algorithm consisting of hidden layers 2010 to generate an output 2011 with the top three (or more) differential diagnoses shows with associated rank order or probability. In the fourth row, a single axial MRI image of the brain 2012 is illustrated with both the 3D cursor and image markup by the radiologist. A 3D cursor, which encapsulates the sub-volume 2013, can be inputted into a deep learning algorithm consisting of hidden layers 2014 to generate an output 2015 with the top three differential diagnoses shows with associated rank order or probability. A single or combination approach (via averaging) can be implemented at the discretion of a radiologist to determine the final reported rank list in his/her report. For example, two approaches can be chosen (such as the top row algorithm utilizing unmarked image sets and the bottom row algorithm using marked image sets and sub-volumes). The unmarked image set approach may be given a ⅓ weighting factor with the differential diagnosis of Abscess (85% probability) and Tumor (15% probability). The radiologist marked, sub-volume approach may be given a ⅔ weighting factor with the differential diagnosis of Abscess (95% probability) and Tumor (5% probability). Thus, the combined probability reported in the radiologist report would be Abscess 91.7% probability and Tumor 8.3% probability.

FIG. 21 illustrates the flow chart of generating a simulated realistic 3D radiological dataset. Step 2100 is a simulation of MRI, CT, PET, SPECT or DTS medical image data through establishing a 3D grid system and associated X, Y, Z coordinate system. Step 2102 is a mathematical process to populate a 3D volume with simulated data corresponding to and representative of MRI, CT, PET or DTS medical images. Step 2104 is assigning a tissue type property to each voxel within the simulated dataset. Step 2106 is potting and displaying the simulated 3D MRI, CT, PET or DTS data. Step 2108 is establishing the 3D cursor with associated functionality. Step 2110 is establishing the process by which the 3D volume of simulated data can be segmented. Step 2112 is establishing the process by which the 3D volume of simulated data can be filtered. Step 2114 is establishing the geo-registered tools with associated functionality. Step 2116 is establishing the adjudication process for times when radiologists/medical personnel diagnoses conflict with AI algorithm diagnoses. Step 2118 is implementing the overall system functionality.

Figure 22:
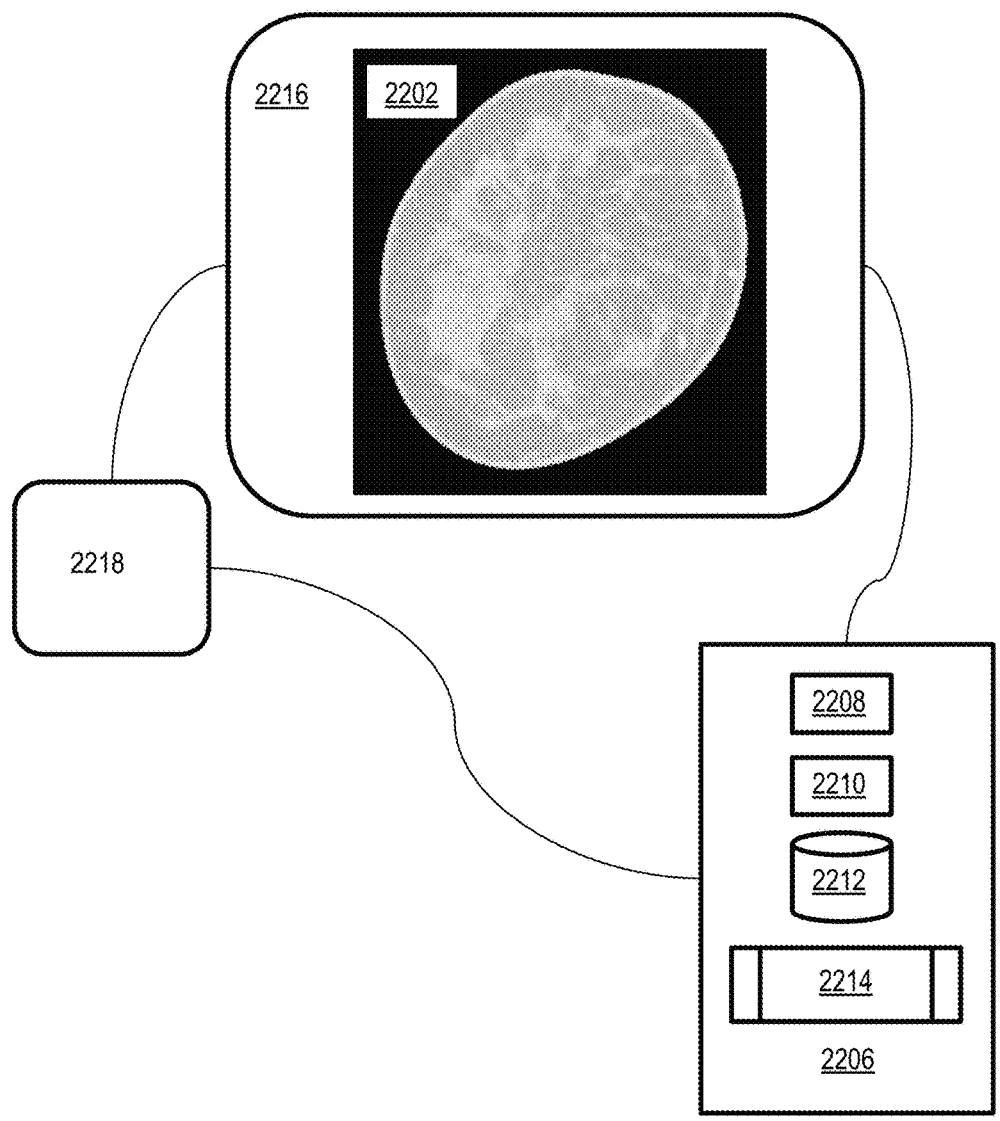
FIG. 22 illustrates the apparatus/system to generate simulated 3D dataset (e.g., MRI, CT, PET, SPECT or DTS data) which could be used to train and test during AI algorithm development and also could be used to train radiologists/medical personnel.

FIG. 22 illustrates the apparatus/system to generate simulated 3D datasets (e.g., MRI, CT, PET, SPECT or DTS data), which could be used to train and test during AI algorithm development and also could be used to train radiologists/medical personnel. A computer is used to generate the medical images 2202 of an anatomic structure (with or without pathology as desired) of interest. The computer contains an image processor 2206, that includes processors 2208 (e.g., CPUs and GPUs), volatile memory 2210 (e.g., RAM), and non-volatile storage 2212 (e.g. HDDs and SSDs). A program 2214 running on the image processor implements one or more steps as described below, e.g. and without limitation to generate simulations. 3D medical images are displayed on an TO device 2216. The TO device may include a virtual reality, mixed reality or augmented reality headset, monitor, tablet computer, PDA (personal digital assistant), mobile phone, or any of a wide variety of devices, either alone or in combination. The TO device may include a touchscreen and may accept input from external devices (represented by 2218) such as a geo-registered tool (e.g., georegistration pen described in USPTO 62/711,658) keyboard, mouse, and any of a wide variety of equipment for receiving various inputs. However, some or all the inputs could be automated, e.g. by the program 2214.

Figure 23A:
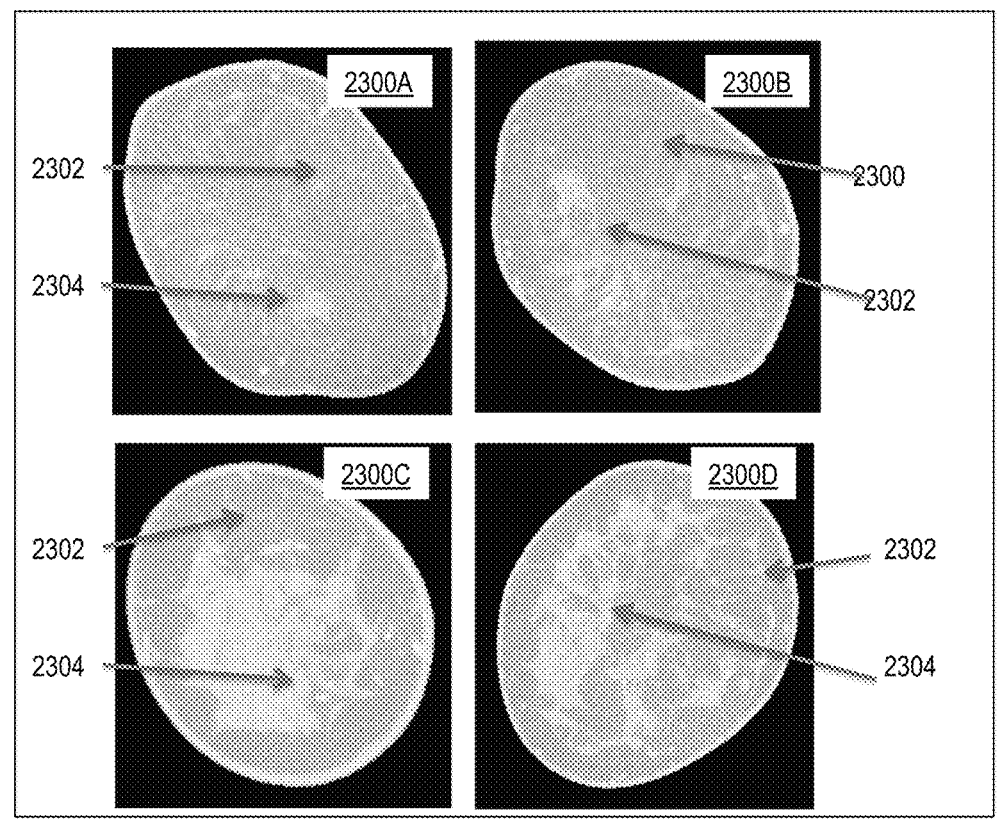
FIG. 23A illustrates 4 CT scans from 4 different breasts, some of which have more fatty composition than others.

FIG. 23A illustrates 4 CT scans from 4 different breasts, some of which have more fatty composition than others. A CT image from a first breast 2300A is shown and is predominantly fatty. Fatty tissue 2302 is shown. Glandular tissue 2304 is shown. A CT image from a second breast 2300B is shown and is predominantly fatty. Fatty tissue 2302 is shown. Glandular tissue 2304 is shown. A CT image from a third breast 2300C is shown and is predominantly fatty. Fatty tissue 2302 is shown. Glandular tissue 2304 is shown. A CT image from a fourth breast 2300D is shown and is predominantly fatty. Fatty tissue 2302 is shown. Glandular tissue 2304 is shown.

Figure 23B:
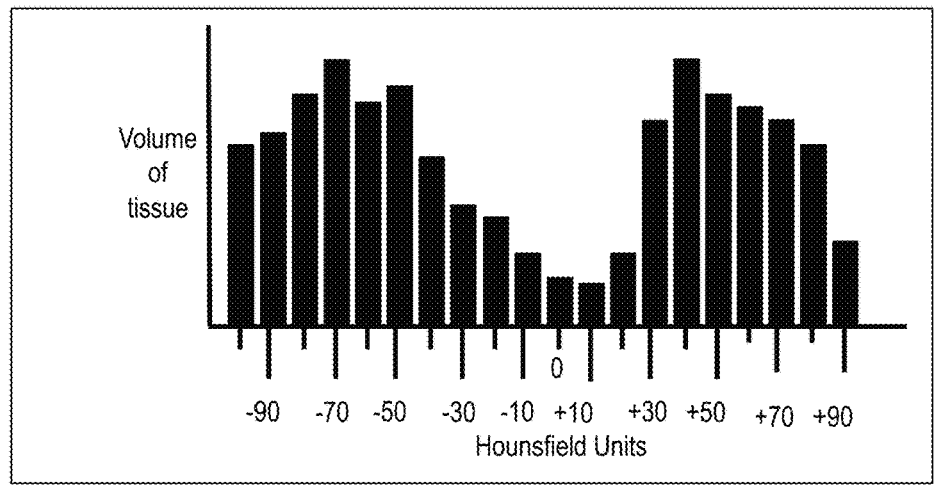
FIG. 23B illustrates a histogram showing variable densities of a breast.

FIG. 23B illustrates a histogram showing variable densities of a breast with distribution of Hounsfield units for glandular density mainly in the range of 30 to 80 Hounsfield Units and the fatty breast tissue mainly in the range of −100 to −30.

Figure 23C:
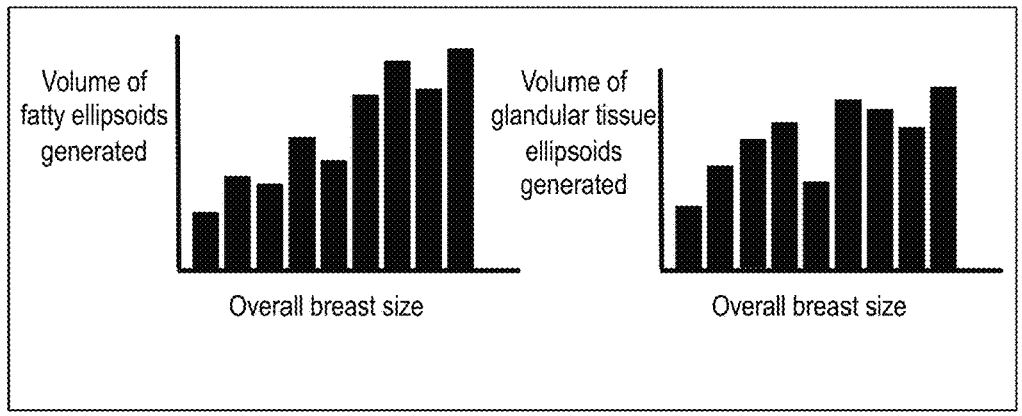
FIG. 23C illustrates an example relationship between fatty tissue ellipsoids generated and overall breast size.

FIG. 23C illustrates an example relationship between fatty tissue ellipsoids generated and overall breast size. Also shown is an example relationship between glandular tissue ellipsoids generated and overall breast size.

Figure 24:
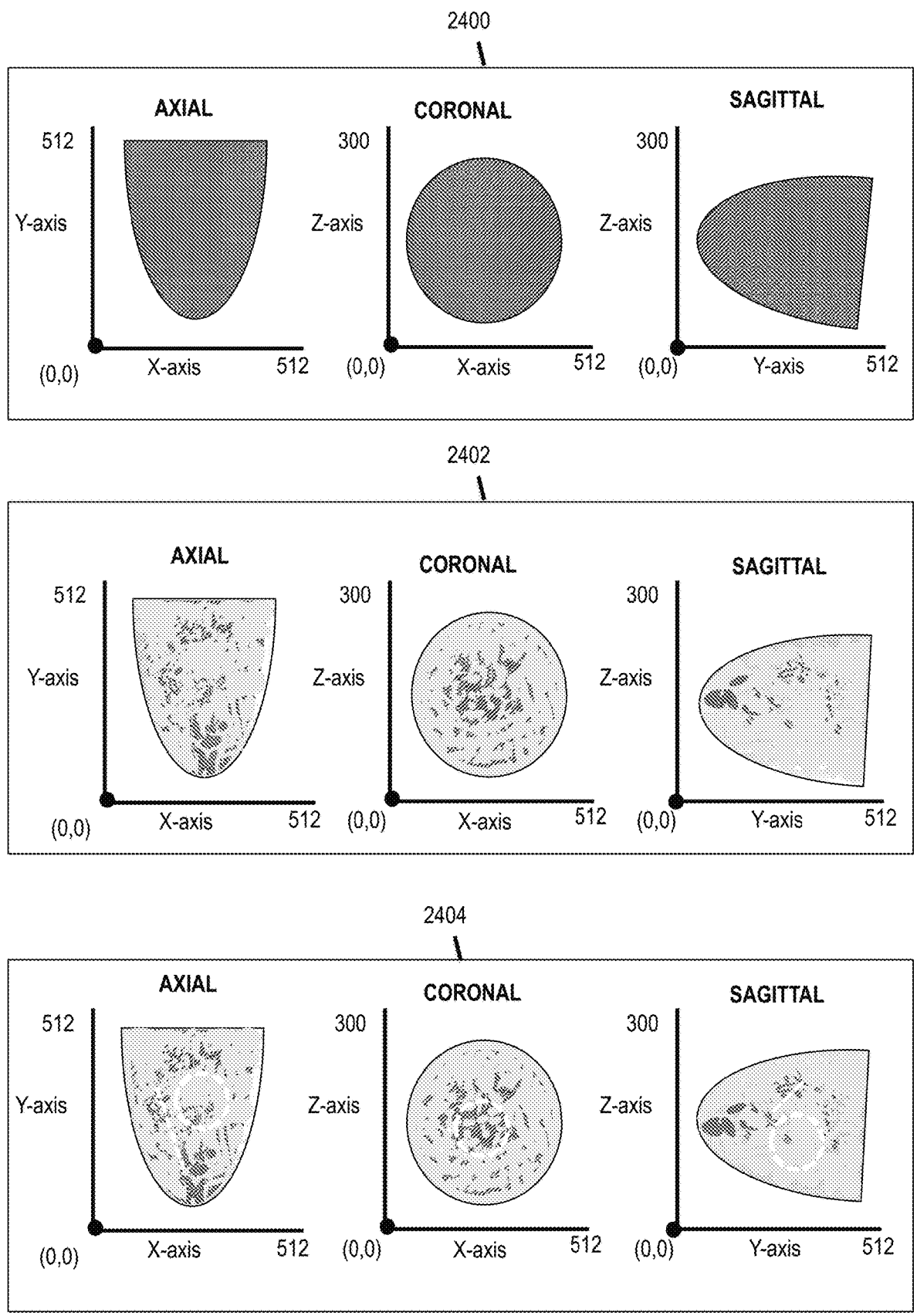
FIG. 24 illustrates generating simulated data of a breast containing microcalcifications as an example.

FIG. 24A illustrates generating simulated data of a breast containing microcalcifications as an example. There would be: different distributions in size and shapes of breasts; different distributions of fatty tissue type and glandular tissue type; different distributions of microcalcifications which includes size of the microcalcifications, number of microcalcification clusters, shapes of the microcalcification clusters, and multiple types of microcalcification clusters within the same patient. For the purposes of this example, we will discuss various sizes, tissue composition (fatty breast tissue versus glandular breast tissue) and the inclusion of simulated microcalcifications with variable patterns thereof (e.g., linear pattern, linear pattern with branch, linear pattern with multiple branches, along the surface of a sphere, randomly distributed). For simplicity of this example, other structures (nipple, skin, blood vessels, implants, etc.) are not discussed, but could be generated by using this process. Additional structures could also be included, such as tumor, abscess or other anatomic structures or pathologies. As a preparatory step, CT and MRI data could be collected and statistics collected regarding the tissue distribution characteristics over a large sample size. Both of these imaging techniques under represent the distribution of micro calcifications, which could be obtained from mammogram data.

The preferred embodiment for is first described for a method to generate the simulated 3D dataset. 2400 illustrates step 1 of filling the breast with glandular breast tissue. Note: X=width; Y=depth; Z=height. Nominal maximum pixels in each direction will be assigned, e.g., X=512; Y pixels=512; and, Z pixels=300. Use nested 'do loops' to fill volume. Based on the dimensions of the breast fix a center point from which a radius can be created to 'round out; the forward corners of the breast. Eliminate the voxels external to this hemisphere. For each voxel, assign a number (e.g., random assignment) to select the density (i.e., Hounsfield unit—uniform distribution Hounsfield units with densities 30-60 units) for each voxel within the breast. Note this fills a breast shaped volume with gray scales distributed in accordance with typical distribution of tissue of normal glandular tissue density. 2402 illustrates step 2 of creating and superimpose fatty tissue within the breast. Create 3D ellipsoids. Note: if one were to examine different breasts, there would be different distributions of fatty tissue both in number and in size of the fatty ellipsoids depending on the person being examined. Also, there is a propensity for the tissue immediately underneath the skin (subcutaneous region) to be fatty. Other patterns could be established as desired. For the medium breast in this case, there would be 100 different ellipsoids generated with randomly selected ellipsoid volumes—small medium large. From historical data, establish the dimensions of small, medium and large fatty ellipsoids. For each of the ellipsoids, a coordinate (i.e., X, Y, Z) of the center point would be randomly selected and, optionally, the spherical angle of the major axis of the ellipsoid. A Hounsfield unit would be selected for each ellipsoid (e.g., randomly selected between −20 to −100). Replace the Hounsfield unit of all the voxels which were generated in Step 1, above which are subtended by voxels of each ellipsoid with the Hounsfield unit of the respective ellipsoids. 2404 step 3 is to create and superimpose microcalcifications within the breast. Create microcalcifications clusters. Randomly distributed pattern—superimpose a near-uniform distribution random number (e.g., 200). For the respective numbers drawn, draw random numbers for each microcalcification's coordinate (X, Y, Z) within the bounds established in Step 1 *a*. Replace the Hounsfield unit of all the voxels which were generated in Step 1, above which are subtended by voxels of microcalcifications with the Hounsfield unit of microcalcifications (nominally 70-200). Spherical cluster pattern—microcalcifications randomly distributed along the surface of a sphere-like shape of variable diameter. Assign random numbers for the location of the sphere center within the bounds established in Step 1 such that the entire sphere can be contained within the breast and not entering the subcutaneous tissue region. Assign a set (e.g., 50 to 100) of random numbers for the coordinate of a microcalcification along the surface of the sphere. Replace the Hounsfield unit of all the voxels which were generated in 2400 Step 1, above which are subtended by voxels of microcalcifications (2404 Step 3) with the Hounsfield unit of microcalcifications. Linear pattern—microcalcifications in a near-linear pattern of variable lengths. Assign a set of linear (or curvilinear) coordinates for each linear (or narrow cylindrical-like) pattern such that the entire line-type structure can be contained within the breast and not entering the subcutaneous region. Assign the coordinates of each microcalcification along the lines for both cases. (Note: if the coordinates of m are not within the bounds established in Step 1 *a*, repeat 2400 Step 3). Replace the Hounsfield unit of all the voxels which were generated in 2400 Step 1, above which are subtended by voxels of microcalcifications (2404 Step 3) with the Hounsfield unit of microcalcifications. Linear with branching pattern—microcalcifications are in a near-linear pattern with branches of variable lengths. Combinations of cases—vary the number of spherical with linear and the number of spherical and linear with branches. (Combinations repeat the above steps based on the combination selected.). There is an option to convert the above data from 3D voxels to 2D pixels (nominally XY planes of 2D data for which there would be Z planes of data (i.e., 2D slices). To further describe this process, the desired dataset can be generated (e.g., breast size and shape, composition, presence of microcalcifications, etc.). The assignment could be via human input or via an AI process. First, assign the breast size (e.g., assigning a size of 1000 cm$^3$). Next, assign the percentage (and distribution) of glandular breast tissue (and corresponding number, size and shape of glandular lobules). Note: voxels may be of variable size, shape, density or other internal property patterns. Next, assign the percentage (and distribution) of fatty breast tissue (and corresponding number, size and shape of glandular lobules). For example, a cluster of 30 voxels arranged in a 3×5×2 (transverse×anterior-posterior by superior-inferior). Since these structures are small volumes being inserted, this approach is referred to as a sub-volume by sub-volume approach.

A random number generator can be utilized to generate the size (e.g., number of voxels in the lobule) and shape (e.g., number of voxels in each row and column determine shape in for a particular slice, but when this is coupled with varying slices, the 3D shape is determined). Note: voxels may be of variable size, shape, density or other internal property patterns. Next, assign microcalcifications with patterns, such as follows: diffuse microcalcifications (variable size, shape and density with a random pattern, but geographically separated relatively uniformly throughout a region of or the entire breast); spherical distribution (microcalcifications of variable size, shape and density randomly distributed along the surface of a sphere-like shape of variable diameter); linear pattern (microcalcifications of variable size, shape and density distributed over a linear-like pattern of variable length to match that of realistic intraductal calcification patterns); and, linear with branching pattern (microcalcifications of variable size, shape and density distributed over a linear and branching pattern of variable length and shape to match that of a intraductal calcification patterns). Note: that there is flexibility in this design, such that for microcalcifications, some of the rows and columns could be empty and some filled with data units corresponding to Hounsfield units of microcalcifications. Note that this is useful for the insertion of artificially generated sets of microcalcifications because those voxels with microcalcifications Hounsfield units would replace those voxels with soft tissue or fat Hounsfield Units and those voxels wherein a particular row/column is empty would not replace those voxels with soft tissue or fat Hounsfield units. For a medium breast (e.g., 500 cm$^3$), a similar to the process for a large breast can be used with a different percentage (and distribution) of fatty breast tissue, glandular breast tissue and microcalcification patterns. For a small breast (e.g., 250 cm$^3$), a similar to the process for a large breast with a different percentage (and distribution) of fatty breast tissue, glandular breast tissue and microcalcification patterns. Note that these datasets can be built by taking sub-volumes of breast tissue (e.g., a group of voxels corresponding to microcalcifications, a group of voxels corresponding to breast fatty tissue, etc.) and inserting them into the large volume of the breast through techniques discussed in U.S. patent application Ser. No. 16/010,925, INTERACTIVE PLACEMENT OF A 3D DIGITAL REPRESENTATION OF A SURGICAL DEVICE OR ANATOMIC FEATURE INTO A 3D RADIOLOGIC IMAGE FOR PRE-OPERATIVE PLANNING and U.S. patent application Ser. No. 16/195,251, INTERACTIVE VOXEL MANIPULATION IN VOLUMETRIC MEDICAL IMAGING FOR VIRTUAL MOTION, DEFORMABLE TISSUE, AND VIRTUAL RADIOLOGICAL DISSECTION. In these patent applications, the insertion of voxels into a dataset is disclosed. Thus, at this point, an entire voxelated dataset is generated.

Next consider and example of how the data would be generated. Generate a half-ellipsoid-like shape boundary for the breast (for the purpose of describing the process, a medium sized breast is shown in this step) with glandular breast tissue (Step 1; FIGS. 4A and 4B), fatty tissue (Step 2; FIG. 4C) and microcalcifications (Step 3; FIG. 4D). No other findings (masses, blood vessels, skin, nipple, implants, etc.) are shown. This would be replicated for the other sizes with their respective dimensions/shapes.

Some embodiments comprise wherein the entire simulated 3D dataset is generated prior to performing a discriminator. Other embodiments comprise wherein a discrimination is applied after each slice is generated, discussed in FIG. 27.

The embodiment wherein sub-volumes are inserted into the volume is the preferred mode. An alternative embodiment of generating a simulated 3D dataset include a slice-by-slice method (2D slices are added sequentially rather than 3D lobules of voxels).

At this juncture, however, it is unknown whether the generated voxelated dataset appears real or whether the generated voxelated dataset appears fake. A discrimination process must be applied.

After a dataset is generated, a discrimination process needs to occur to determine whether the dataset appears real or whether the dataset appears fake. For example, assume that the generated simulated 3D dataset through processes described above is a breast CT. The preferred embodiment is to perform a discrimination process on each 2D axial slice, then each 2D coronal slice, then each 2D sagittal slice. In a first preferred embodiment, if the volume is determined to appear real on all axial slices, all coronal slices and all sagittal slices, then the simulated 3D dataset is determined to be real. The slices could be shown to the discriminator in using varying window and level settings. Alternative embodiments include performing discriminator on axial images only. Alternative embodiments include performing discriminator on coronal images only. Alternative embodiments include performing discriminator on sagittal images only. Alternative embodiments include performing discriminator on oblique images. Alternative embodiments include performing discriminator on post-processed images (e.g., window/level adjustments, segmented and filtered images, maximum intensity projection images, or other types of images). Another alternative embodiment is to perform all 3 planes (axial, sagittal, coronal) with multiple post-processing images would serve as a more stringent discriminator and will result in more realistic simulated 3D datasets; however, this requires high computing demand.

Figure 25:
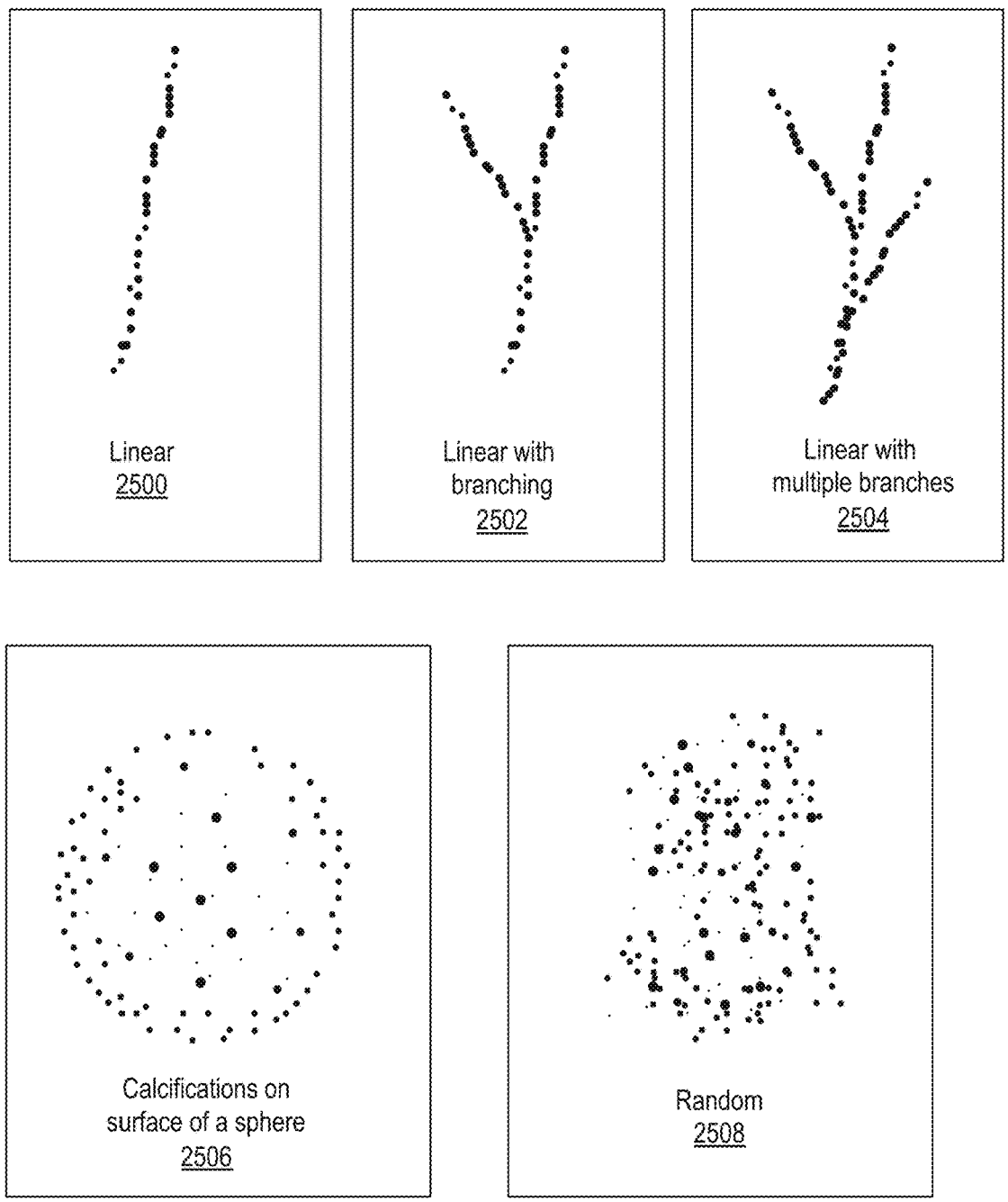
FIG. 25 illustrates groupings of micro calcifications within a breast.

FIG. 25 illustrates varying patterns of AI generated microcalcifications. Note is made that these datasets can be sparse voxel datasets and inputted into the dataset of the breast via replacement of existing voxels with new microcalcification voxels. To further describe the sparse voxel dataset, some (x,y,z) coordinates are plotted with microcalcifications and other (x,y,z) coordinates are left empty with no data unit. These microcalcifications can be rotated and inserted in a fashion to best mimic anatomic and pathologic conditions. A linear pattern 2500 is illustrated. A linear with branching pattern 2502 is illustrated. A linear with multiple branches pattern 2504 is illustrated. A calcifications on surface of sphere pattern 2506 is illustrated. A random pattern 2508 is illustrated.

Figure 26:
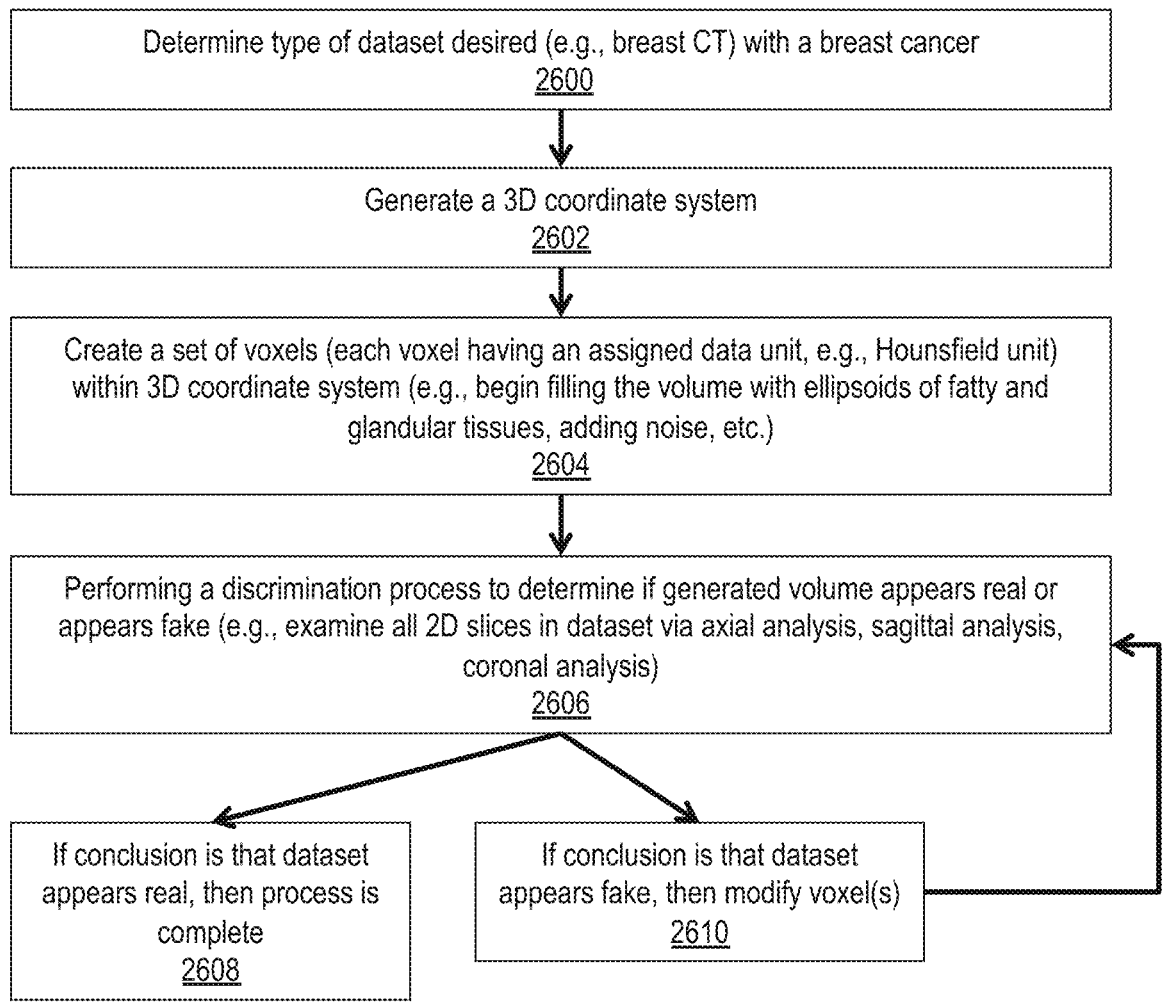
FIG. 26 is a flow chart for generating a simulated realistic 3D dataset.

FIG. 26 is a flow chart for generating a simulated realistic 3D dataset. Step 2600 is to determine type of dataset desired (e.g., breast CT) with a breast cancer. Step 2602 is to generate a 3D coordinate system. Step 2604 is to create a set of voxels (each voxel having an assigned data unit, e.g., Hounsfield unit) within 3D coordinate system (e.g., begin filling the volume with ellipsoids of fatty and glandular tissues, adding noise, etc.). Step 2606 is to perform a discrimination process to determine if generated volume appears real or appears fake (e.g., examine all 2D slices in dataset via axial analysis, sagittal analysis, coronal analysis). Step 2610 is if the discrimination process determines that dataset appears fake to then modify voxel(s). Then, step 2606 is repeated. Step 2608 is to complete the dataset if the discrimination process determines that the generated volume appears real.

Figure 27:
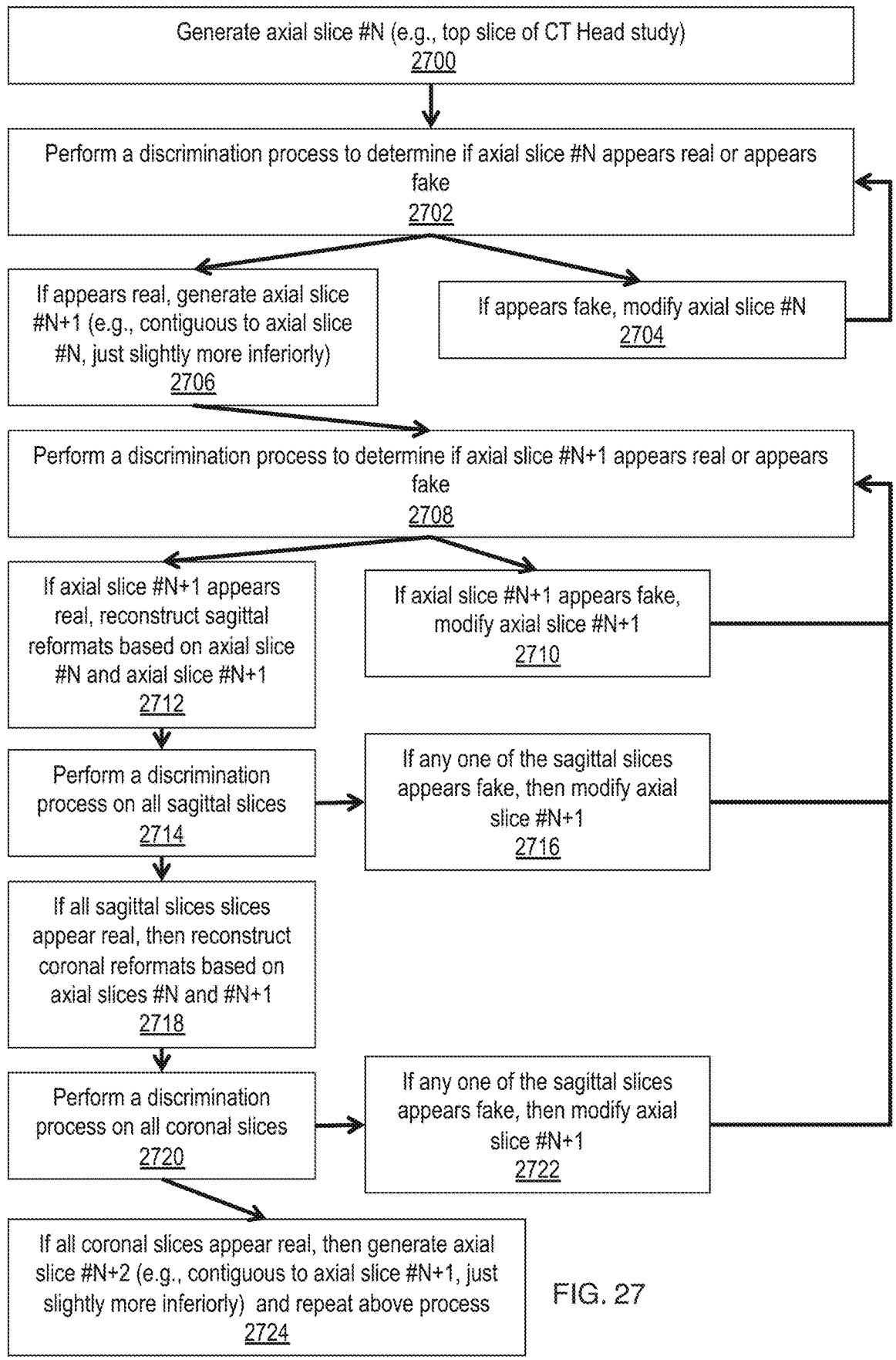
FIG. 27 illustrates a flowchart for generating a simulated realistic 3D radiological dataset interleaving a discriminator into a slice-by-slice generation process.

FIG. 27 illustrates a flowchart for generating a simulated realistic 3D radiological dataset interleaving a discriminator into a slice-by-slice generation process. This is referred to as a layer-by-layer approach. Step 2700 is to generate axial slice #N (e.g., top slice of CT Head study). Step 2702 is to perform a discrimination process to determine if axial slice #N appears real or appears fake. Step 2704 is to modify axial slice #N if axial slice N is determined to be fake. Step 2706 is to generate axial slice #N+1 (e.g., contiguous to axial slice #1, just slightly more inferiorly) if slice #N is thought to be real. Step 2708 is to perform a discrimination process to determine if axial slice #N+1 appears real or appears fake. Step 2710 is to modify axial slice #N+1 if axial slice #N+1 is determined to appear fake. Step 2712 is if axial slice #N+1 appears real, reconstruct sagittal reformats based on axial slice #N and axial slice #N+1. Step 2714 is to perform a discrimination process on all sagittal slices. Step 2716 is if any one of the sagittal slices appears fake to then modify axial slice #N+1. Step 2718 is if all sagittal slices appears real to then reconstruct coronal reformats based on axial slices #N and #N+1. Step 2720 is to perform a discrimination process on all coronal slices. Step 2722 is if any one of the sagittal slices appears fake to then modify axial slice #N+1. Step 2724 is if all coronal slices appear real, then generate axial slice #N+2 (e.g., contiguous to axial slice #N+1, just slightly more inferiorly) and repeat above process. Thus, this process discloses a way to strategically build the dataset layer-by-layer wherein each layer is determined to be real appearing prior to adding the next layer.

In the event that one of the 2D slices appears fake, only voxels corresponding to that particular slice are modified. A single 2D axial slice of the data could be run through a discrimination process (e.g., as is done in generative adversarial networks). Reconstructions (e.g., coronal and sagittal images) performed and the discrimination process performed on those reconstructions. If the dataset appears real based on the coronal and sagittal images, then the process is completed and the axial image can then be added to the dataset.

Also, please note that if this layer-by-layer approach is not performed, an additional embodiment is disclosed on providing options on how to accurately build the simulated 3D dataset if the discriminator determines that if the simulated 3D dataset appears fake. For example, voxel(s) in the dataset can be modified and a discrimination process will be reapplied. This process can undergo iterations until the discriminator determines that the 3D volume appears real. Additionally, if the discriminator determines that the 3D volume of the entire dataset can be discarded.

Note that multiple datasets (e.g., training dataset, validation dataset, testing dataset) could be generated to test performance of machine learning algorithms for improved diagnosis, such as is described in PCT/US2019/023968, Radiologist-assisted machine learning with interactive, volume-subtending 3d cursor. Note: at this juncture there would be available both 2D data and a corresponding set of 3D data. Parameters used above (e.g., the number of microcalcifications, sizes of clusters, type of distribution) are illustrative and could be easily modified to reflect a 'typical breast'. Furthermore, whole CT, MRI scans of the head, neck, chest, abdomen, pelvis and extremity can be performed using methods disclosed. For training and testing of AI algorithms, much larger data sets would be generated.

FIG. 28 illustrates a lobule of fat generated through artificial intelligence. Such a lobule would be used in conjunction with the volume-by-volume approach. A top slice 2800 of the lobule of fat is shown in the table below. A bottom slice 2802 of the lobule of fat is shown in the table below.

The invention claimed is:

1. A method of generating simulated volumetric datasets comprising:
   generating a 3D coordinate system;
   generating a simulated 3D dataset comprising a set of voxels wherein each voxel within said set of voxels has an assigned data unit within said 3D coordinate system comprising:
      generating a sub-volume, wherein the sub-volume includes a pathologic feature;
      inserting said sub-volume into the 3D coordinate system;
   performing a discrimination process on said simulated 3D dataset wherein said discrimination process determines whether said simulated 3D dataset appears real or appears fake; and
   modifying voxel(s) within said simulated 3D dataset when said discrimination process determines that said simulated 3D dataset appears fake.

2. The method of claim 1 further comprising wherein said generating a simulated 3D dataset comprises wherein at least one additional pathologic structures are inserted into said simulated 3D dataset wherein said at least one additional pathologic structure is different from said pathologic structure.

3. The method claim 1 further comprises performing analysis of a set of real medical imaging examinations to generate metrics.

4. The method of claim 3 wherein said performing analysis comprises at least one of the group consisting of: calculating a mean; calculating a median; calculating a mode; calculating a standard deviation; calculating a variance; calculating a histogram type analysis; and, performing advanced statistical methods to characterize the data.

5. The method of claim 3 further comprising wherein said discrimination process of said simulated 3D dataset compares metrics of said simulated 3D dataset with metrics of the set of real medical imaging examinations.

6. The method of claim 5 further comprising wherein said simulated dataset is modified under conditions wherein the metrics of said simulated dataset differ from the metrics of said real imaging examinations.

7. The method of claim 1 further comprising wherein generating a simulated 3D dataset utilizes a layer-by-layer approach.

8. The method of claim 7 further comprising wherein said sub-volumes further comprises at least one of the group consisting of: insertion of real sub-volumes from actual data into said simulated 3D dataset; insertion of simulated 3D sub-volumes into said simulated 3D dataset; and, insertion of simulated 3D sub-volumes into actual patient examinations.

9. The method of claim 1 further comprising wherein performing a discrimination process on said simulated 3D dataset utilizes at least one of the group consisting of: AI analysis of reformatted images from multiple contiguous slices; and, AI analysis of processed images including maximum intensity projection images and volume rendering images.

10. The method of claim 1 further comprising wherein said simulated 3D dataset comprises at least one of the group consisting of: a single anatomic structure; an age-specific normal examination; a gender-specific examination; and, varying pathologic conditions.

11. The method of claim 10 further comprising wherein a difficulty level is established associated with some particular pathology for testing purposes wherein said difficulty level is related to at least one of the group consisting of: a size of a lesion; a conspicuity of lesion; a presence of imaging artifacts; and, a frequency of disease.

12. The method of claim 1 further comprising wherein said simulated 3D dataset comprises at least one of the group consisting of: a simulation of pathologic growth occurs over time; and, a simulation of a changing imaging feature.

13. The method of claim 1 further comprising wherein said simulated 3D dataset is used for medical education in a time-step interactive process performing the steps of:
  selecting the demographics of the patient;
  selecting the pathology;
  selecting the imaging examination; and
  modifying said medical imaging examination to simulate pathology.

14. The method of claim 13 further comprising wherein said pathology comprises one of the group consisting of: tumor(s); infection(s); traumatic injury (ies); and, other known diseases.

15. The method of claim 1 further comprising wherein a user provides feedback to denote the fake appearing region through use of a 3D volume cursor.

16. A method comprising:
  using a generative adversarial network to create a first image slice and insert a pathologic feature into said first image slice;
  performing a discrimination process to determine if said first image slice appears real;
  if said first image slice appears real, using a generative adversarial network to create at least one additional image slice wherein said at least one additional image slice is contiguous with said first image slice;
  performing the discrimination process to determine if the at least one additional image slice appears real;
  if the at least one additional image slice appears real:
    arranging said first image slice and said at least one additional image slice to generate a volume; and
    reconstructing a reformat from said volume wherein said reformat contains at least a portion of said first slice and at least a portion of said at least one additional image slice; and
  performing a discrimination process on said reformat.

17. The method of claim 16 further comprising wherein said reformat comprises at least one of the group consisting of: an axial image; a sagittal image; a coronal image; and, an oblique image.

18. A method comprising:
  using an artificial intelligence (AI) process to create a first image slice and insert a pathologic feature into said first image slice;
  performing a discrimination process to determine if said first image slice appears real;
  if said first image slice appears real, using an AI process to create at least one additional image slice wherein said at least one additional image slice is contiguous with said first image slice;
  performing the discrimination process to determine if the at least one additional image slice appears real;
  if the at least one additional image slice appears real:
    arranging said first image slice and said at least one additional image slice to generate a volume; and
    reconstructing a reformat from a said volume wherein said reformat contains at least a portion of said first slice and at least a portion of said at least one additional image slice; and
  performing a discrimination process on said reformat.

19. The method of claim 18 further comprising wherein said reformat comprises at least one of the group consisting of: an axial image; a sagittal image; a coronal image; and, an oblique image.

20. The method of claim 18 further comprising wherein a user provides feedback to denote the fake appearing region through use of a 3D volume cursor.

* * * * *